United States Patent
Fernandez Prieto et al.

(10) Patent No.: US 8,236,748 B2
(45) Date of Patent: *Aug. 7, 2012

(54) PH TUNEABLE AMIDO-GELLANT FOR USE IN CONSUMER PRODUCT COMPOSITIONS

(75) Inventors: Susana Fernandez Prieto, Benicarlo-Castellon (ES); Johan Smets, Lubbeek (BE); Beatriu Escuder Gil, Sant Mateu-Castello (ES); Juan Felipe Miravet Celades, Castellon (ES); Vincent Josep Nebot Carda, Vila real-Castellon (ES)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/045,768

(22) Filed: Mar. 11, 2011

(65) Prior Publication Data
US 2011/0224124 A1    Sep. 15, 2011

(51) Int. Cl.
C11D 1/02    (2006.01)
C11D 1/66    (2006.01)
C11D 3/32    (2006.01)

(52) U.S. Cl. .......... 510/501; 564/152; 564/153
(58) Field of Classification Search .......... 510/501; 564/152, 153
See application file for complete search history.

(56) References Cited

U.S. PATENT DOCUMENTS

| | | | |
|---|---|---|---|
| 4,623,471 A | 11/1986 | Wilsberg | |
| 5,286,406 A | 2/1994 | Scholz et al. | |
| 5,707,952 A | 1/1998 | Lambremont et al. | |
| 7,018,642 B2 | 3/2006 | Degenhardt et al. | |
| 7,332,529 B2 * | 2/2008 | Carr | 516/20 |
| 7,534,915 B2 | 5/2009 | van Bommel et al. | |
| 7,708,982 B2 | 5/2010 | O'Leary et al. | |
| 7,910,526 B2 | 3/2011 | Kakizaki et al. | |
| 2004/0247664 A1 | 12/2004 | Dreja et al. | |
| 2006/0089416 A1 | 4/2006 | Carr | |
| 2008/0057005 A1 | 3/2008 | Lehn et al. | |
| 2008/0096780 A1 | 4/2008 | Veugelers et al. | |

FOREIGN PATENT DOCUMENTS

| | | |
|---|---|---|
| DE | 20 43 088 A1 | 3/1972 |
| DE | 10136950 A1 | 2/2003 |
| EP | 0 077 674 A2 | 4/1983 |
| WO | WO 97/17963 A1 | 5/1997 |
| WO | WO 99/15610 A1 | 4/1999 |
| WO | WO 2008/102127 A2 | 8/2008 |

OTHER PUBLICATIONS

Barnes, D.J.; Chapman, R.L.; Vagg, R.S.; Watton, E.C., J. Chem. Eng. Data 1978, 23(4), 349-350.
Moll, Maria . Acta Pol. Pharm: 1968, 25(4), 367-373 (Pol).
Sukuzi, M. Tetrahedron Letters, Elsevier, Amsterdam 45 (2004) 5399-5402.
Estroff, Lara; Hamilton, Andrew;Chemical Reviews, vol. 104, No. 3, Jan. 1, 2004, 1201-1218.
International Search report dated Mar. 11, 2011 containing 8 pages.

(Continued)

Primary Examiner — Gregory Delcotto
(74) Attorney, Agent, or Firm — Melissa G Krasovec; Leonard W Lewis

(57) ABSTRACT

The invention is to pH tunable amido-gellant that are suitable for use in consumer product compositions.

6 Claims, 1 Drawing Sheet

OTHER PUBLICATIONS

International Search Report dated Mar. 11, 2011 containing 7 pages for U.S. Appl. No. 13/045,749.

Becerril, J.;Bolte, M.; Burguete, M.I.; Galindo, F.; Garcia-Espana, E.; Luis, S. V.; Miravet J. F. J Am. Chem. Soc. 2003, 125, 6677-6686.

* cited by examiner

PH TUNEABLE AMIDO-GELLANT FOR USE IN CONSUMER PRODUCT COMPOSITIONS

FIELD OF THE INVENTION

The present invention relates to structurants that are compatible with a broad range of detergent compositions and does not affect product clarity.

BACKGROUND OF THE INVENTION

Today's consumers desire high performance liquid detergent compositions having sufficient structuring to give a rich impression and stabilize performance ingredients. External structurants for providing rheological benefits to consumer product compositions include those derived from castor oil, fatty acids, fatty esters, or fatty soap water-insoluble waxes. However, the required performance ingredients often complicate the addition of external structurants known in the art and may even be incompatible with them. For instance, many external structurants are degraded by performance ingredients, such as enzymes, including protease and lipase (lipase hydrolyses ester bonds present in castor oil derivatives), which are desirable for improved low temperature cleaning. They are also often incompatible with low pH and peroxide bleaches. In addition, external structurants generally require the use of structurant premixes incorporating large amounts of water. Such structurant premixes are unsuitable for compact detergents and for unit-dose applications.

Amido-gellants provide a solution for structuring consumer product compositions while also being compatible with a broad range of optional detergent ingredients, such as bleaches and/or enzymes. They also provide an aesthetically pleasing pour profile without negatively impacting the composition clarity. They can be formulated into structurant premixes that are entirely water-free. However, most amido-gellants require premixes that have to be heated to as high as 100° C. to reduce the viscosity to a level where they can be easily mixed with a detergent composition. Since ingredients such as enzymes and perfumes start to degrade at temperatures as low as 50° C., they must be added after the amido-gellant, and after a cooling step.

As such, a need remains for a structurant for consumer product compositions, that is compatible with a broad range of ingredients (including heat-sensitive ingredients such as enzymes), while also being easy to incorporate in to the composition without requiring excessive heating.

SUMMARY OF THE INVENTION

The present invention is to a pH tunable amido-gellant having a formula selected from the group consisting of:

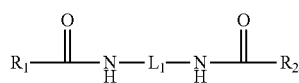
[I]

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group.

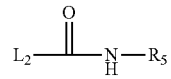
[II]

wherein $R_5$ is an aminofunctional moiety; $L_2$ is a backbone moiety having molecular weight from 14 to 500 g/mol; and at least one of $L_2$ or $R_5$ comprises a pH-sensitive group;
and mixtures thereof;
wherein the pH tunable amido-gellant has a pKa of from 1 to 30, and with the exclusion that the di-amido gellant is not a protein.

Another aspect of the present invention relates to the use of such pH tunable amido-gellant for structuring consumer product compositions, preferably fluid detergent compositions.

DETAILED DESCRIPTION OF THE INVENTION

Figure 1:
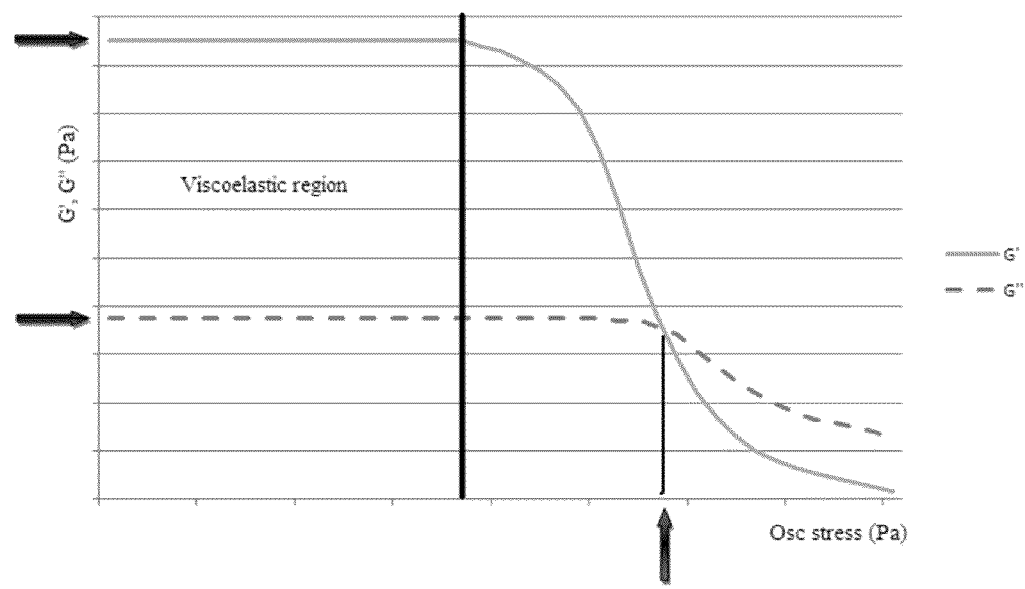
FIG. 1 details G' and G" within the linear viscoelastic region and the oscillation stress at the point where G' and G" cross over as a measure for gel strength.

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

The pH-tunable amido gellants are particularly useful for consumer product compositions having a fluid form, particularly liquid and gel forms. Such fluid forms also include fluid detergent compositions. Fluid detergent compositions as described herein include but are not limited to consumer products such as: shampoos; skin cleaners and exfolients; shaving liquids, foams and gels; products for treating fabrics, hard surfaces and any other surfaces in the area of fabric and home care, including: dishwashing, laundry cleaning, laundry and rinse additives, hard surface cleaning including floor and toilet bowl cleaners; products relating to oral care including toothpastes and gels and whiteners. A particularly preferred embodiment is a "fluid laundry detergent composition". As used herein, "fluid laundry detergent composition" refers to any laundry treatment composition comprising a fluid capable of wetting and cleaning fabric e.g., clothing, in a domestic washing machine.

The consumer product composition can include solids or gases in suitably subdivided form, but the overall composition excludes product forms which are non-fluid overall, such as tablets or granules. The consumer product compositions preferably have densities in the range from of 0.9 to 1.3 grams per cubic centimeter, more preferably from 1.00 to 1.10 grams per cubic centimeter, excluding any solid additives but including any bubbles, if present.

The consumer product compositions may be opaque, semi-transparent or even clear. When clarity of the consumer product composition is desired, the consumer product composition has a turbidity of from 5 NTU to less than 3000 NTU, preferably less than 1000 NTU, more preferably less than 500 NTU and most preferably less than 100 NTU.

All percentages, ratios and proportions used herein are by weight percent of the composition, unless otherwise specified. All average values are calculated "by weight" of the composition or components thereof, unless otherwise expressly indicated.

External Structurant:

The external structurant preferably imparts a shear thinning viscosity profile to the consumer product composition, independently from, or extrinsic from, any structuring effect of the detersive surfactants of the composition. Preferred external structurants include those which provide a pouring viscosity from 50 cps to 20,000 cps, more preferably from 200 cps to 10,000 cps, most preferably from 500 cps to 7,000 cps. The consumer product composition preferably has a resting viscosity of at least 1,500 cps, preferably at least 10,000 cps, more preferably at least 50,000 cps. This resting (low stress) viscosity represents the viscosity of the consumer product composition under gentle shaking in the package and during transportation. Alternatively, the consumer product composition may be a thixotropic gel. Such compositions may have a resting viscosity of from 10,000 cps to 500,000 cps, preferably from 100,000 cps to 400,000 cps, more preferably from 200,000 to 300,000. The preferred shear-thinning characteristics of the consumer product is defined as a ratio of low stress viscosity to pouring viscosity of at least 2, preferably at least 10, more preferably at least 100, up to 2000.

The pouring viscosity is measured at a shear rate of 20 sec$^{-1}$, which is a shear rate that the consumer product composition is typically exposed to during pouring. The resting (low stress) viscosity is determined under a constant stress of 0.1 Pa during a viscosity creep experiment over a 5 minute interval. Rheology measurements over the 5 minute interval are made after the composition has rested at zero shear rate for at least 10 minutes, between loading the sample in the rheometer and running the test. The data over the last 3 minutes are used to fit a straight line, and from the slope of this line, the low stress viscosity is calculated. The viscosity is measured at 21° C. using a TA AR 2000 (or AR G2) rheometer with a 40 mm stainless steel plate having a gap of 500 microns.

1. pH Tunable Amido Gellant

The pH tunable amido gellant provides the consumer product composition with a viscosity profile that is dependent on the pH of the composition. The pH tunable amido gellants comprise at least one pH sensitive group. When a pH tunable amido gellant is added to a polar protic solvent such as water, it is believed that the nonionic species form the viscosity building network while the ionic species are soluble and do not form a viscosity building network. By increasing or decreasing the pH (depending on the selection of the pH-sensitive groups) the amido gellant is either protonated or deprotonated. Thus, by changing the pH of the solution, the solubility, and hence the viscosity building behaviour, of the amido gellant can be controlled. By careful selection of the pH-sensitive groups, the pKa of the amido gellant can be tailored. Hence, the choice of the pH-sensitive groups can be used to select the pH at which the amido gellant builds viscosity.

The consumer product composition comprises from 0.01 wt % to 10 wt %, preferably from 0.05 wt % to 5 wt %, more preferably from 0.1 wt % to 2 wt %, most preferably from 0.4 wt % to 1 wt %, of a pH tunable amido-gellant as an external structuring system. In an alternative embodiment, the consumer product composition comprises from 0.1 wt % to 0.5 wt % of the pH tunable amido-gallant. The pH tunable amido-gellant has a formula selected from the group consisting of:

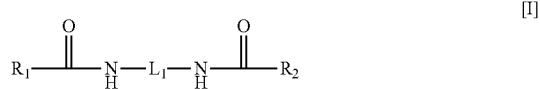
[I]

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group.

[II]

wherein $R_5$ is an aminofunctional moiety; $L_2$ is a backbone moiety having molecular weight from 14 to 500 g/mol; and at least one of $L_2$ or $R_5$ comprises a pH-sensitive group;

and mixtures thereof;

wherein the pH tunable amido-gellant has a pKa of from 1 to 30, preferably a pKa of from 1.5 to 14.

The pH tunable amido gellant comprises at least one amido functional group, and further comprises at least one pH-sensitive group. Preferably, the pH tunable amido gellant has a molecular weight from 150 to 1500 g/mol, more preferably from 300 g/mol to 900 g/mol, most preferably from 400 g/mol to 700 g/mol.

In one embodiment, the pH tunable amido gellant has the following structure [I]:

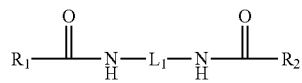

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group.

$L_1$ preferably has the formula:

$$L_1 = A_a - B_b - C_c - D_d,$$ III wherein: (a+b+c+d) is from 1 to 20; and A, B, C and D are independently selected from the linking groups consisting of:

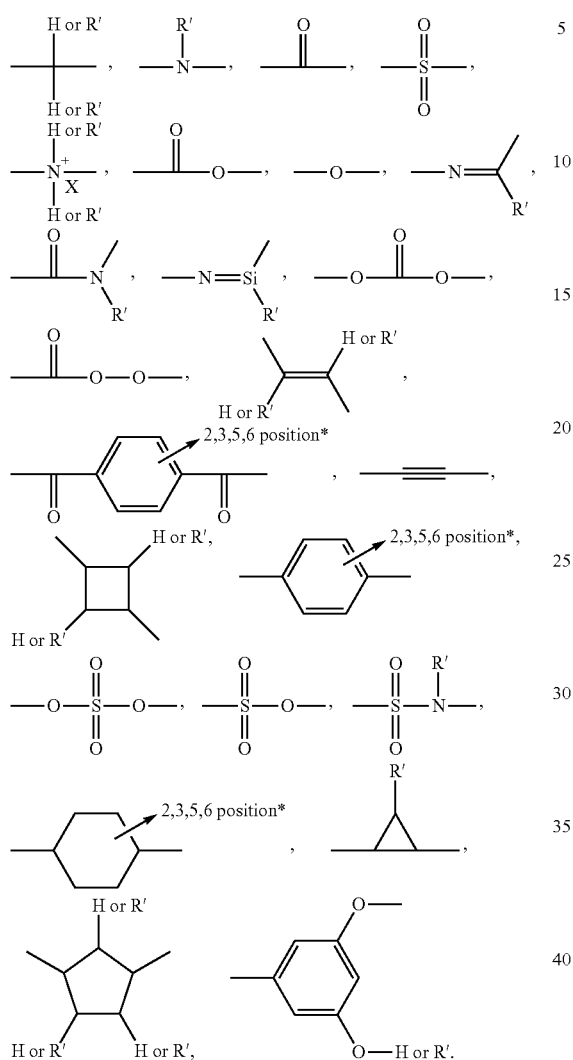

Preferably, A, B, C and D are independently selected from the linking groups consisting of:

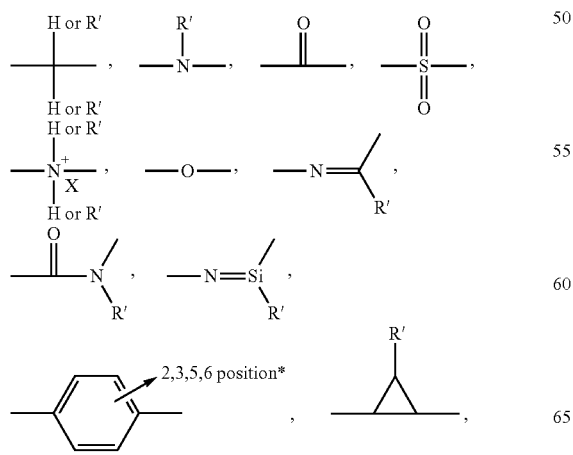

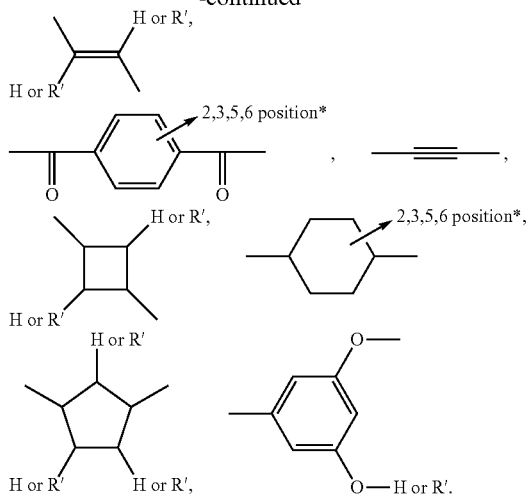

*the arrow indicates up to 4 substitutions in the positions indicated, and $X^-$ an anion Preferably, $L_1$ is selected from C2 to C20 hydrocarbyl chains, more preferably C6 to C12, most preferably C8 to C10.

In a preferred embodiment: $R_1$ is $R_3$ or

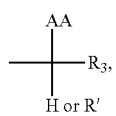

$R_2$ is $R_4$ or

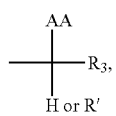

wherein each AA is independently selected from the group consisting of:

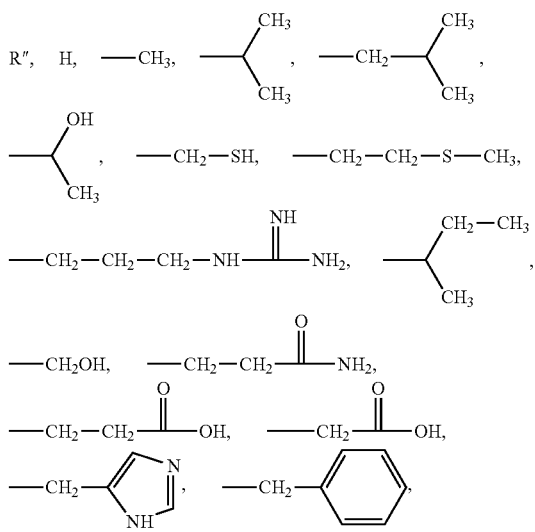

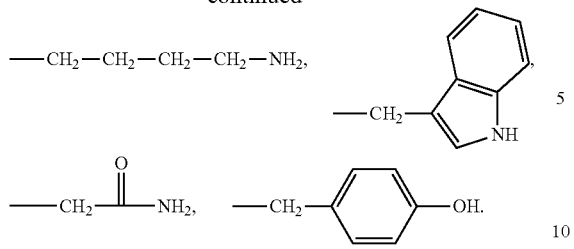

and $R_3$ and $R_4$ independently have the formula:

$$(L')_o\text{-}(L'')_q\text{—}R, \qquad [IV]$$

wherein: (o+q) is from 1 to 10; L' and L" are linking groups, independently selected from the same groups as A, B, C and D in equation [III]; and R, R' and R" are independently selected either from the pH-sensitive-groups consisting of:

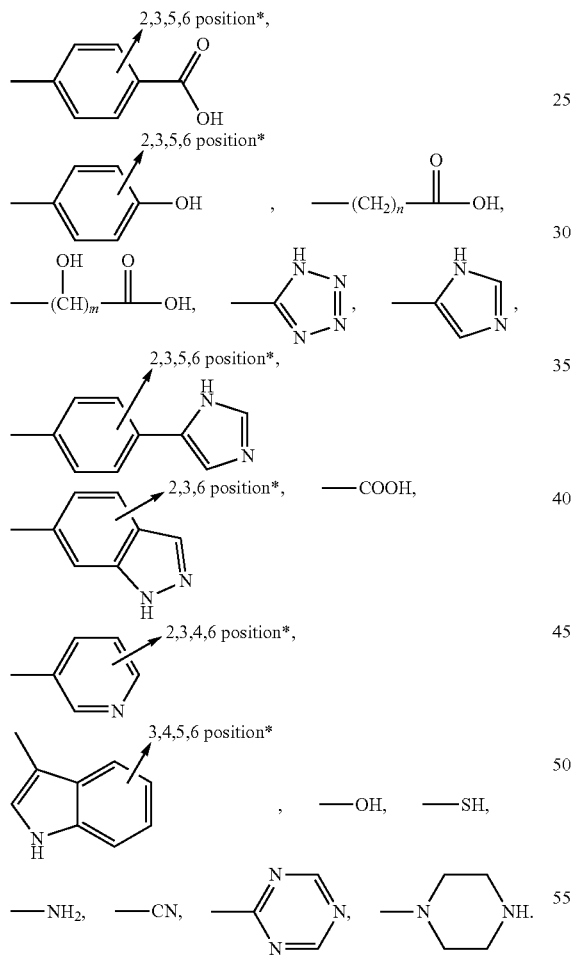

*the arrow indicates up to 4 substitutions in the positions indicated, n and m are integers from 1 to 20 or from the non-pH-sensitive groups consisting of:

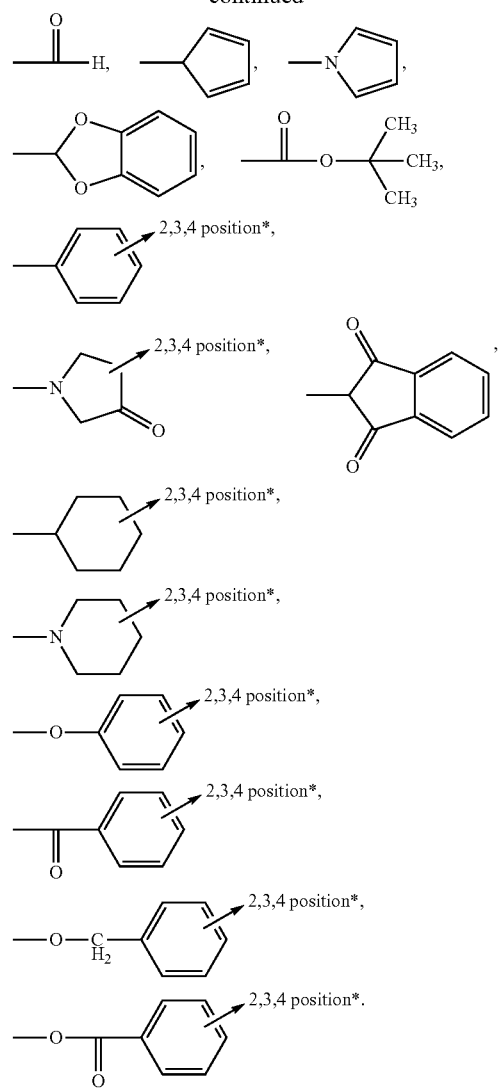

such that at least one of R, R' and R" comprises a pH-sensitive group. Preferably, R comprises the pH-sensitive group.

In other embodiments, at least some of R, R' and R" are independently selected from the group of pH-sensitive molecules consisting of:

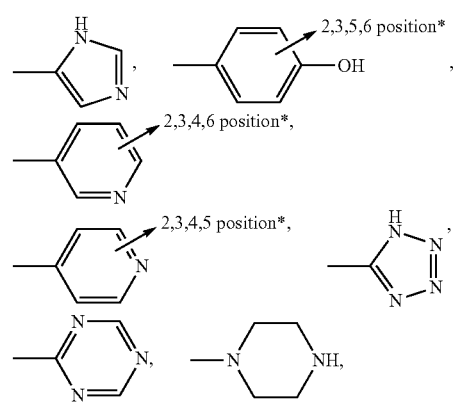

-continued

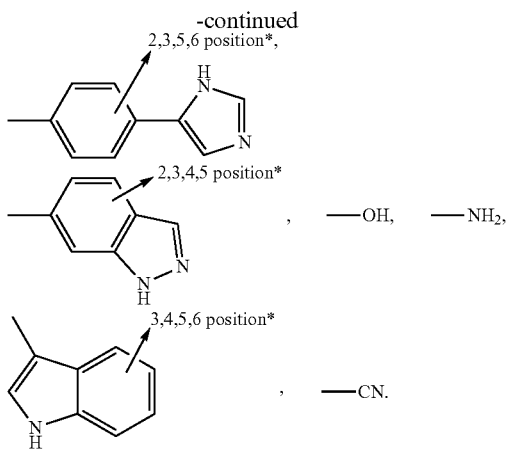

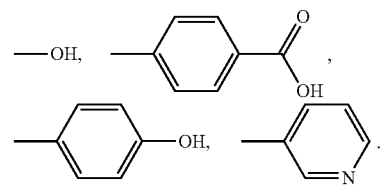

or from the group:

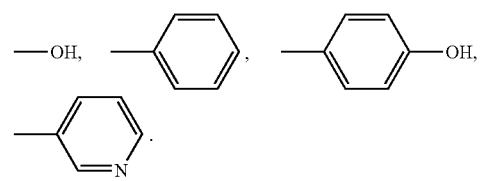

In a preferred embodiment, the pH tunable amido gellant having structure [I] is characterized in that: $L_1$ is an aliphatic linking group with a backbone chain of from 2 to 20 carbon atoms, preferably —$(CH_2)_n$— wherein n is selected from 2 to 20, and both $R_1$ and $R_2$ have the structure:

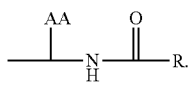

AA is preferably selected from the group consisting of:

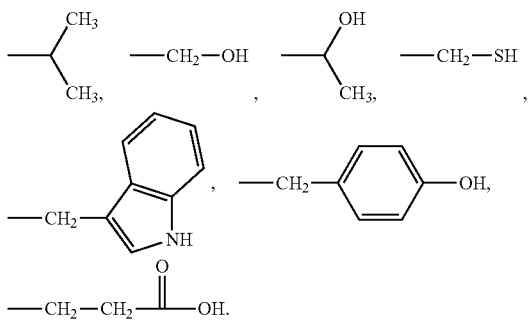

or from the group consisting of:

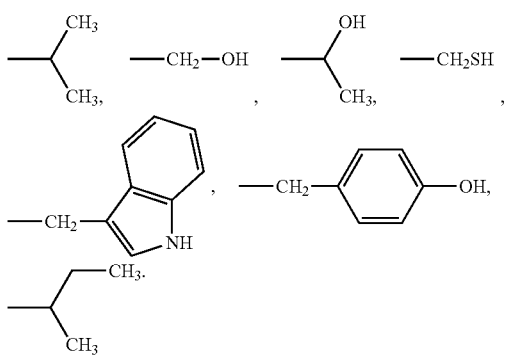

and R is preferably selected from the pH-sensitive groups consisting of:

In another embodiment, two or more of $L_1$, L' and L" are the same group.

The pH tunable amido gellant molecule described in formula [I] can be symmetric with respect to the $L_1$ entity or can be asymmetric. Without intending to be bound by theory, it is believed that symmetric pH tunable amido gellant molecules allow for more orderly structured networks to form, whereas compositions comprising one or more asymmetric pH tunable amido gellant molecules can create disordered networks.

Suitable pH tunable amido gellants having structure [I] may be selected from table 1 and table 2, table 3, and mixtures thereof. More preferably, the pH tunable amido gellants, having structure [I], are selected from table 2, and mixtures thereof. Alternatively, the pH tunable amido gellants, having structure [I], are selected from table 3, and mixtures thereof.

In another embodiment, the pH tunable amido gellant has the structure [II]:

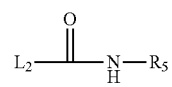

wherein $R_5$ is an aminofunctional moiety; $L_2$ is a backbone moiety having molecular weight from 14 to 500 g/mol; and at least one of $L_2$ or $R_5$ comprises a pH-sensitive group;

$L_2$ preferably has the formula:

$$L_2 = A_a - B_b - C_c - D_d - R''' \qquad [V]$$

wherein: (a+b+c+d) is from 1 to 20; and R''' is either a pH-sensitive group or a non-pH-sensitive groups (selected from the same groups as R, R' and R" for structure [I]).

Preferably, $L_2$ is selected from C2 to C20 hydrocarbyl chains, more preferably C6 to C12, most preferably C8 to C10.

$R_5$ preferably has the formula:

[V]

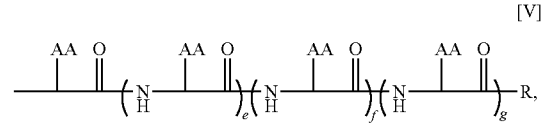

wherein: AA is independently selected from the same group of AA as for structure [I]; (e+f+g) is from 0 to 20, more preferably from 1 to 3.

At least one of AA, R or R''' comprises a pH sensitive group. Preferably, R comprises the pH sensitive group.

In a preferred embodiment, the pH tunable amido gellant having structure [II] is characterized in that: $L_2$ is an aliphatic linking group with a backbone chain of from 2 to 20 carbon atoms, preferably —$(CH_2)_n$—$CH_3$ wherein n is selected from 2 to 20, and $R_5$ has the structure:

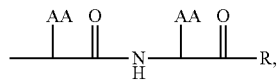

wherein: each AA is independently selected from the group consisting of:

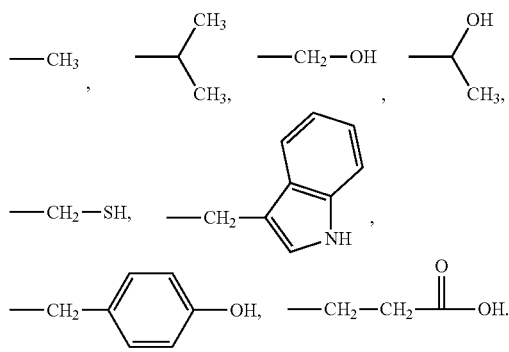

or from the group consisting of:

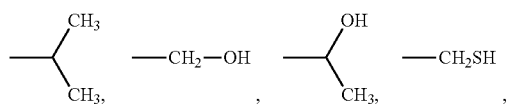

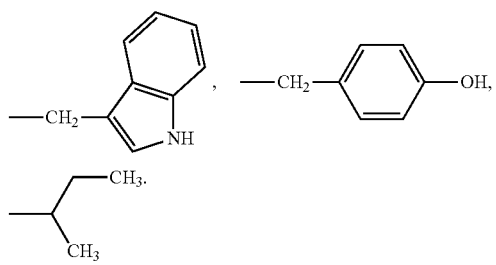

and R is selected from the pH-sensitive groups consisting of:

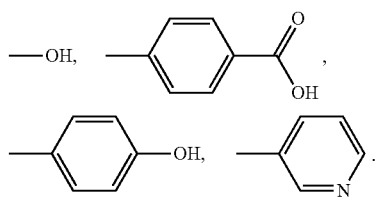

or from the group:

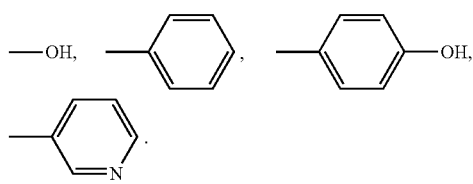

Suitable pH tunable amido gellants having structure [II] include the structures selected from Table 4, and mixtures thereof.

pH Tunable Amido Gellant Examples of The Present Invention:

TABLE 1

Non-limiting examples of pH tuneable amido gellants having structure [I]:

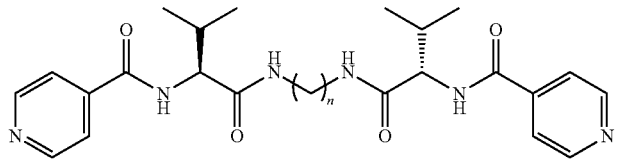

| | |
|---|---|
| N,N'-(2S,2'S)-1,1'-(ethane-1,2-diylbis(azanediyl))bis(3-methyl-1-oxobutane-2,1-diyl)diisonicotinamide | N,N'-(2S,2'S)-1,1'-(propane-1,3-diylbis(azanediyl))bis(3-methyl-1-oxobutane-2,1-diyl)diisonicotinamide |
| N,N'-(2S,2'S)-1,1'-(butane-1,4-diylbis(azanediyl))bis(3-methyl-1-oxobutane-2,1-diyl)diisonicotinamide | N,N'-(2S,2'S)-1,1'-(pentane-1,5-diylbis(azanediyl))bis(3-methyl-1-oxobutane-2,1-diyl)diisonicotinamide |
| N,N'-(2S,2'S)-1,1'-(hexane-1,6-diylbis(azanediyl))bis(3-methyl-1-oxobutane-2,1-diyl)diisonicotinamide | N,N'-(2S,2'S)-1,1'-(heptane-1,7-diylbis(azanediyl))bis(3-methyl-1-oxobutane-2,1-diyl)diisonicotinamide |
| N,N'-(2S,2'S)-1,1'-(octane-1,8-diylbis(azanediyl))bis(3-methyl-1-oxobutane-2,1-diyl)diisonicotinamide | |

TABLE 1-continued

Non-limiting examples of pH tuneable amido gellants having structure [I]:

(6S,13S)-6,13-diisopropyl-4,7,12,15-tetraoxo-5,8,11,14-tetraazaoctadecane-1,18-dioic acid
(6S,15S)-6,15-diisopropyl-4,7,14,17-tetraoxo-5,8,13,16-tetraazaeicosane-1,20-dioic acid
(6S,17S)-6,17-diisopropyl-4,7,16,19-tetraoxo-5,8,15,18-tetraazadocosane-1,22-dioic acid
(6S,19S)-6,19-diisopropyl-4,7,18,21-tetraoxo-5,8,17,20-tetraazatetracosane-1,24-dioic acid
(6S,21S)-6,21-diisopropyl-4,7,20,23-tetraoxo-5,8,19,22-tetraazahexacosane-1,26-dioic acid
(6S,23S)-6,23-diisopropyl-4,7,22,25-tetraoxo-5,8,21,24-tetraazaoctacosane-1,28-dioic acid (6S,14S')-6,14-diisopropyl-4,7,13,16-tetraoxo-5,8,12,15-tetraazanonadecane-1,19-dioic acid
(6S,16S)-6,16-diisopropyl-4,7,15,18-tetraoxo-5,8,14,17-tetraazaheneicosane-1,21-dioic acid
(6S,18S)-6,18-diisopropyl-4,7,17,20-tetraoxo-5,8,16,19-tetraazatricosane-1,23-dioic acid
(6S,20S)-6,20-diisopropyl-4,7,19,22-tetraoxo-5,8,18,21-tetraazapentacosane-1,25-dioic acid
(6S,22S)-6,22-diisopropyl-4,7,21,24-tetraoxo-5,8,20,23-tetraazaheptacosane-1,27-dioic acid N,N'-(2S,2'S)-1,1'-(ethane-1,2-diylbis(azanediyl))bis(3-methyl-1-oxobutane-2,1-diyl)bis(4-(1H-imidazol-5-yl)benzamide)
N,N'-(2S,2'S)-1,1'-(butane-1,4-diylbis(azanediyl))bis(3-methyl-1-oxobutane-2,1-diyl)bis(4-(1H-imidazol-5-yl)benzamide)
N,N'-(2S,2'S)-1,1'-(hexane-1,6-diylbis(azanediyl))bis(3-methyl-1-oxobutane-2,1-diyl)bis(4-(1H-imidazol-5-yl)benzamide)
N,N'-(2S,2'S)-1,1'-(octane-1,8-diylbis(azanediyl))bis(3-methyl-1-oxobutane-2,1-diyl)bis(4-(1H-imidazol-5-yl)benzamide)
N,N'-(2S,2'S)-1,1'-(decane-1,10-diylbis(azanediyl))bis(3-methyl-1-oxobutane-2,1-diyl)bis(4-(1H-imidazol-5-yl)benzamide)
N,N'-(2S,2'S)-1,1'-(dodecane-1,12-diylbis(azanediyl))bis(3-methyl-1-oxobutane-2,1-diyl)bis(4-(1H-imidazol-5-yl)benzamide)

N,N'-(2S,2'S)-1,1'-(propane-1,3-diylbis(azanediyl))bis(3-methyl-1-oxobutane-2,1-diyl)bis(4-(1H-imidazol-5-yl)benzamide)
N,N'-(2S,2'S)-1,1'-(pentane-1,5-diylbis(azanediyl))bis(3-methyl-1-oxobutane-2,1-diyl)bis(4-(1H-imidazol-5-yl)benzamide)
N,N'-(2S,2'S)-1,1'-(heptane-1,7-diylbis(azanediyl))bis(3-methyl-1-oxobutane-2,1-diyl)bis(4-(1H-imidazol-5-yl)benzamide)
N,N'-(2S,2'S)-1,1'-(nonane-1,9-diylbis(azanediyl))bis(3-methyl-1-oxobutane-2,1-diyl)bis(4-(1H-imidazol-5-yl)benzamide)
N,N'-(2S,2'S)-1,1'-(undecane-1,11-diylbis(azanediyl))bis(3-methyl-1-oxobutane-2,1-diyl)bis(4-(1H-imidazol-5-yl)benzamide)

TABLE 2

Non-limiting examples of pH tuneable amido gellants having structure [I]:

N,N'-(2S,2'S)-1,1'-(nonane-1,9-diylbis(azanediyl))bis(3-methyl-1-oxobutane-2,1-diyl)diisonicotinamide
N,N'-(2S,2'S)-1,1'-(undecane-1,11-diylbis(azanediyl))bis(3-methyl-1-oxobutane-2,1-diyl)diisonicotinamide
N,N'-(2S,2'S)-1,1'-(tridecane-1,13-diylbis(azanediyl))bis(3-methyl-1-oxobutane-2,1-diyl)diisonicotinamide
N,N'-(2S,2'S)-1,1'-(hexadecane-1,16-diylbis(azanediyl))bis(3-methyl-1-oxobutane-2,1-diyl)diisonicotinamide N,N'-(2S,2'S)-1,1'-(decane-1,10-diylbis(azanediyl))bis(3-methyl-1-oxobutane-2,1-diyl)diisonicotinamide
N,N'-(2S,2'S)-1,1'-(dodecane-1,12-diylbis(azanediyl))bis(3-methyl-1-oxobutane-2,1-diyl)diisonicotinamide
N,N'-(2S,2'S)-1,1'-(tetradecane-1,14-diylbis(azanediyl))bis(3-methyl-1-oxobutane-2,1-diyl)diisonicotinamide
N,N'-(2S,2'S)-1,1'-(octadecane-1,18-diylbis(azanediyl))bis(3-methyl-1-oxobutane-2,1-diyl)diisonicotinamide TABLE 2-continued Non-limiting examples of pH tuneable amido gellants having structure [I]:

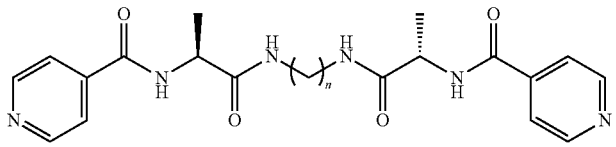

N,N'-(2S,2'S)-1,1'-(ethane-1,2-diylbis(azanediyl))bis(1-oxopropane-2,1-diyl)diisonicotinamide
N,N'-(2S,2'S)-1,1'-(butane-1,4-diylbis(azanediyl))bis(1-oxopropane-2,1-diyl)diisonicotinamide
N,N'-(2S,2'S)-1,1'-(hexane-1,6-diylbis(azanediyl))bis(1-oxopropane-2,1-diyl)diisonicotinamide
N,N'-(2S,2'S)-1,1'-(octane-1,8-diylbis(azanediyl))bis(1-oxopropane-2,1-diyl)diisonicotinamide
N,N'-(2S,2'S)-1,1'-(decane-1,10-diylbis(azanediyl))bis(1-oxopropane-2,1-diyl)diisonicotinamide
N,N'-(2S,2'S)-1,1'-(dodecane-1,12-diylbis(azanediyl))bis(1-oxopropane-2,1-diyl)diisonicotinamide
N,N'-(2S,2'S)-1,1'-(tetradecane-1,14-diylbis(azanediyl))bis(1-oxopropane-2,1-diyl)diisonicotinamide
N,N'-(2S,2'S)-1,1'-(octadecane-1,18-diylbis(azanediyl))bis(1-oxopropane-2,1-diyl)diisonicotinamide N,N'-(2S,2'S)-1,1'-(propane-1,3-diylbis(azanediyl))bis(1-oxopropane-2,1-diyl)diisonicotinamide
N,N'-(2S,2'S)-1,1'-(pentane-1,5-diylbis(azanediyl))bis(1-oxopropane-2,1-diyl)diisonicotinamide
N,N'-(2S,2'S)-1,1'-(heptane-1,7-diylbis(azanediyl))bis(1-oxopropane-2,1-diyl)diisonicotinamide
N,N'-(2S,2'S)-1,1'-(nonane-1,9-diylbis(azanediyl))bis(1-oxopropane-2,1-diyl)diisonicotinamide
N,N'-(2S,2'S)-1,1'-(undecane-1,11-diylbis(azanediyl))bis(1-oxopropane-2,1-diyl)diisonicotinamide
N,N'-(2S,2'S)-1,1'-(tridecane-1,13-diylbis(azanediyl))bis(1-oxopropane-2,1-diyl)diisonicotinamide
N,N'-(2S,2'S)-1,1'-(hexadecane-1,16-diylbis(azanediyl))bis(1-oxopropane-2,1-diyl)diisonicotinamide

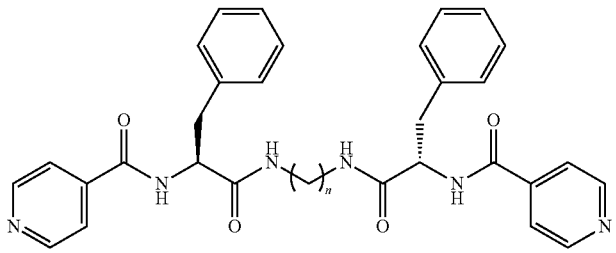

N,N'-(2S,2'S)-1,1'-(ethane-1,2-diylbis(azanediyl))bis(1-oxo-3-phenylpropane-2,1-diyl)diisonicotinamide
N,N'-(2S,2'S)-1,1'-(butane-1,4-diylbis(azanediyl))bis(1-oxo-3-phenylpropane-2,1-diyl)diisonicotinamide
N,N'-(2S,2'S)-1,1'-(hexane-1,6-diylbis(azanediyl))bis(1-oxo-3-phenylpropane-2,1-diyl)diisonicotinamide
N,N'-(2S,2'S)-1,1'-(octane-1,8-diylbis(azanediyl))bis(1-oxo-3-phenylpropane-2,1-diyl)diisonicotinamide
N,N'-(2S,2'S)-1,1'-(decane-1,10-diylbis(azanediyl))bis(1-oxo-3-phenylpropane-2,1-diyl)diisonicotinamide
N,N'-(2S,2'S)-1,1'-(dodecane-1,12-diylbis(azanediyl))bis(1-oxo-3-phenylpropane-2,1-diyl)diisonicotinamide
N,N'-(2S,2'S)-1,1'-(tetradecane-1,14-diylbis(azanediyl))bis(1-oxo-3-phenylpropane-2,1-diyl)diisonicotinamide
N,N'-(2S,2'S)-1,1'-(octadecane-1,18-diylbis(azanediyl))bis(1-oxo-3-phenylpropane-2,1-diyl)diisonicotinamide N,N'-(2S,2'S)-1,1'-(propane-1,3-diylbis(azanediyl))bis(1-oxo-3-phenylpropane-2,1-diyl)diisonicotinamide
N,N'-(2S,2'S)-1,1'-(pentane-1,5-diylbis(azanediyl))bis(1-oxo-3-phenylpropane-2,1-diyl)diisonicotinamide
N,N'-(2S,2'S)-1,1'-(heptane-1,7-diylbis(azanediyl))bis(1-oxo-3-phenylpropane-2,1-diyl)diisonicotinamide
N,N'-(2S,2'S)-1,1'-(nonane-1,9-diylbis(azanediyl))bis(1-oxo-3-phenylpropane-2,1-diyl)diisonicotinamide
N,N'-(2S,2'S)-1,1'-(undecane-1,11-diylbis(azanediyl))bis(1-oxo-3-phenylpropane-2,1-diyl)diisonicotinamide
N,N'-(2S,2'S)-1,1'-(tridecane-1,13-diylbis(azanediyl))bis(1-oxo-3-phenylpropane-2,1-diyl)diisonicotinamide
N,N'-(2S,2'S)-1,1'-(hexadecane-1,16-diylbis(azanediyl))bis(1-oxo-3-phenylpropane-2,1-diyl)diisonicotinamide

TABLE 3

Non-limiting examples of other pH tuneable amido gellants having structure [I]:

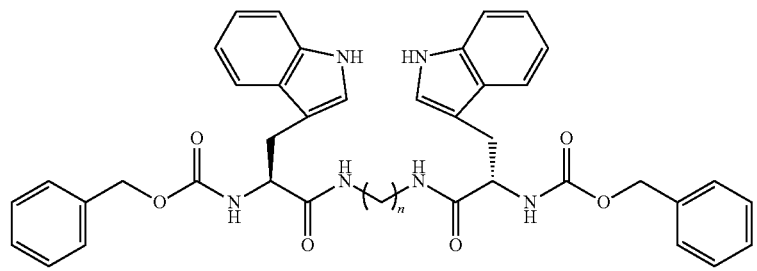

[1-{2-[2-Benzyloxycarbonylamino-3-(1H-indol-3-yl)-propionylamino]-ethylcarbamoyl}-2-(1H-indol-3-yl)-ethyl]-carbamic acid benzyl ester

[1-{3-[2-Benzyloxycarbonylamino-3-(1H-indol-3-yl)-propionylamino]-propylcarbamoyl}-2-(1H-indol-3-yl)-ethyl]-carbamic acid benzyl ester

[1-{4-[2-Benzyloxycarbonylamino-3-(1H-indol-3-yl)-propionylamino]-butylcarbamoyl}-2-(1H-indol-3-yl)-ethyl]-carbamic acid benzyl ester

[1-{5-[2-Benzyloxycarbonylamino-3-(1H-indol-3-y)-propionylamino]-pentylcarbamoyl}-2-(1H-indol-3-yl)-ethyl]-carbamic acid benzyl ester

[1-{6-[2-Benzyloxycarbonylamino-3-(1H-indol-3-yl)-propionylamino]-hexylcarbamoyl}-2-(1H-indol-3-yl)-ethyl]-carbamic acid benzyl ester

[1-{7-[2-Benzyloxycarbonylamino-3-(1H-indol-3-yl)-propionylamino]-heptylcarbamoyl}-2-(1H-indol-3-y)-ethyl]-carbamic acid benzyl ester

[1-{8-[2-Benzyloxycarbonylamino-3-(1H-indol-3-yl)-propionylamino]-octylcarbamoyl}-2-(1H-indol-3-yl)-ethyl]-carbamic acid benzyl ester

[1-{9-[2-Benzyloxycarbonylamino-3-(1H-indol-3-yl)-propionylamino]-nonylcarbamoyl}-2-(1H-indol-3-yl)-ethyl]-carbamic acid benzyl ester

[1-{10-[2-Benzyloxycarbonylamino-3-(1H-indol-3-yl)-propionylamino]-decylcarbamoyl}-2-(1H-indol-3-yl)-ethyl]-carbamic acid benzyl ester

[1-{11-[2-Benzyloxycarbonylamino-3-(1H-indol-3-yl)-propionylamino]-undecylcarbamoyl}-2-(1H-indol-3-yl)-ethyl]-carbamic acid benzyl ester

[1-{12-[2-Benzyloxycarbonylamino-3-(1H-indol-3-yl)-propionylamino]-dodecylylcarbamoyl}-2-(1H-indol-3-yl)-ethyl]-carbamic acid benzyl ester

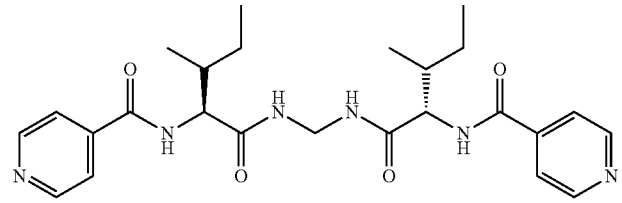

N-[(1S)-2-methyl-1-[2-[[(2S)-3-methyl-2-(pyridine-4-carbonylamino)pentanoyl]amino]ethylcarbamoyl]butyl]pyridine-4-carboxamide N-[(1S)-2-methyl-1-[3-[[(2S)-3-methyl-2-(pyridine-4-carbonylamino)pentanoyl]amino]propylcarbamoyl]butyl]pyridine-4-carboxamide N-[(1S)-2-methyl-1-[4-[[(2S)-3-methyl-2-(pyridine-4-carbonylamino)pentanoyl]amino]butylcarbamoyl]butyl]pyridine-4-carboxamide N-[(1S)-2-methyl-1-[5-[[(2S)-3-methyl-2-(pyridine-4-carbonylamino)pentanoyl]amino]pentylcarbamoyl]butyl]pyridine-4-carboxamide N-[(1S)-2-methyl-1-[6-[[(2S)-3-methyl-2-(pyridine-4-carbonylamino)pentanoyl]amino]hexylcarbamoyl]butyl]pyridine-4-carboxamide N-[(1S)-2-methyl-1-[7-[[(2S)-3-methyl-2-(pyridine-4-carbonylamino)pentanoyl]amino]heptylcarbamoyl]butyl]pyridine-4-carboxamide N-[(1S)-2-methyl-1-[8-[[(2S)-3-methyl-2-(pyridine-4-carbonylamino)pentanoyl]amino]octylcarbamoyl]butyl]pyridine-4-carboxamide N-[(1S)-2-methyl-1-[9-[[(2S)-3-methyl-2-(pyridine-4-carbonylamino)pentanoyl]amino]nonylcarbamoyl]butyl]pyridine-4-carboxamide N-[(1S)-2-methyl-1-[10-[[(2S)-3-methyl-2-(pyridine-4-carbonylamino)pentanoyl]amino]decylcarbamoyl]butyl]pyridine-4-carboxamide N-[(1S)-2-methyl-1-[11-[[(2S)-3-methyl-2-(pyridine-4-carbonylamino)pentanoyl]amino]undecylcarbamoyl]butyl]pyridine-4-carboxamide N-[(1S)-2-methyl-1-[12-[[(2S)-3-methyl-2-(pyridine-4-carbonylamino)pentanoyl]amino]dodecylcarbamoyl]butyl]pyridine-4-carboxamide TABLE 3-continued Non-limiting examples of other pH tuneable amido gellants having structure [I]:

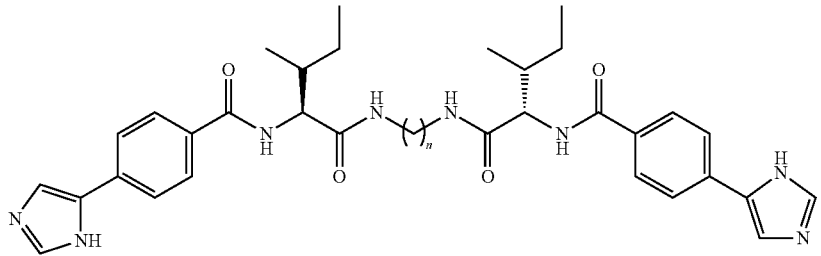

4-(1H-imidazol-5-yl)-N-[(1S)-1-[2-[[(2S)-2-[[4-(1H-imidazol-5-yl)benzoyl]amino]-3-methyl-pentanoyl]amino]ethylcarbamoyl]-2-methyl-butyl]benzamide
4-(1H-imidazol-5-yl)-N-[(1S)-1-[3-[[(2S)-2-[[4-(1H-imidazol-5-yl)benzoyl]amino]-3-methyl-pentanoyl]amino]propylcarbamoyl]-2-methyl-butyl]benzamide
4-(1H-imidazol-5-yl)-N-[(1S)-1-[4-[[(2S)-2-[[4-(1H-imidazol-5-yl)benzoyl]amino]-3-methyl-pentanoyl]amino]butylcarbamoyl]-2-methyl-butyl]benzamide
4-(1H-imidazol-5-yl)-N-[(1S)-1-[5-[[(2S)-2-[[4-(1H-imidazol-5-yl)benzoyl]amino]-3-methyl-pentanoyl]amino]pentylcarbamoyl]-2-methyl-butyl]benzamide
4-(1H-imidazol-5-yl)-N-[(1S)-1-[6-[[(2S)-2-[[4-(1H-imidazol-5-yl)benzoyl]amino]-3-methyl-pentanoyl]amino]hexylcarbamoyl]-2-methyl-butyl]benzamide
4-(1H-imidazol-5-yl)-N-[(1S)-1-[7-[[(2S)-2-[[4-(1H-imidazol-5-yl)benzoyl]amino]-3-methyl-pentanoyl]amino]heptylcarbamoyl]-2-methyl-butyl]benzamide 4-(1H-imidazol-5-yl)-N-[(1S)-1-[8-[[(2S)-2-[[4-(1H-imidazol-5-yl)benzoyl]amino]-3-methyl-pentanoyl]amino]octylcarbamoyl]-2-methyl-butyl]benzamide
4-(1H-imidazol-5-yl)-N-[(1S)-1-[9-[[(2S)-2-[[4-(1H-imidazol-5-yl)benzoyl]amino]-3-methyl-pentanoyl]amino]nonylcarbamoyl]-2-methyl-butyl]benzamide
4-(1H-imidazol-5-yl)-N-[(1S)-1-[10-[[(2S)-2-[[4-(1H-imidazol-5-yl)benzoyl]amino]-3-methyl-pentanoyl]amino]decylcarbamoyl]-2-methyl-butyl]benzamide
4-(1H-imidazol-5-yl)-N-[(1S)-1-[11-[[(2S)-2-[[4-(1H-imidazol-5-yl)benzoyl]amino]-3-methyl-pentanoyl]amino]undecylcarbamoyl]-2-methyl-butyl]benzamide
4-(1H-imidazol-5-yl)-N-[(1S)-1-[12-[[(2S)-2-[[4-(1H-imidazol-5-yl)benzoyl]amino]-3-methyl-pentanoyl]amino]dodecylcarbamoyl]-2-methyl-butyl]benzamide

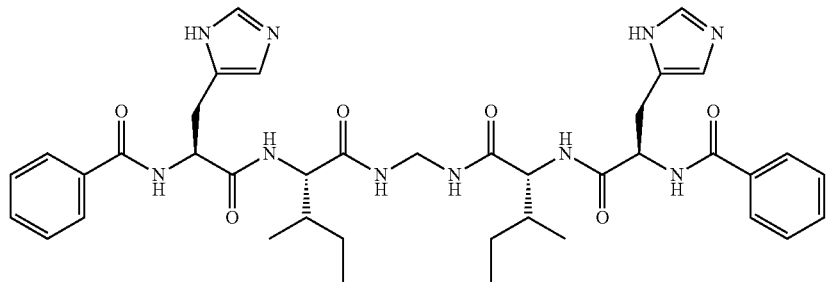

N-[(1S)-2-[[(1S)-1-[[[(2R)-2-[[(2R)-2-benzamido-3-(1H-imidazol-5-yl)propanoyl]amino]-3-methyl-pentanoyl]amino]methylcarbamoyl]-2-methyl-butyl]amino]-1-(1H-imidazol-5-ylmethyl)-2-oxo-ethyl]benzamide
N-[(1R)-2-[[(1R)-1-[3-[[(2S)-2-[[(2S)-2-benzamido-3-(1H-imidazol-5-yl)propanoyl]amino]-3-methyl-pentanoyl]amino]propylcarbamoyl]-2-methyl-butyl]amino]-1-(1H-imidazol-5-ylmethyl)-2-oxo-ethyl]benzamide
N-[(1R)-2-[[(1R)-1-[4-[[(2S)-2-[[(2S)-2-benzamido-3-(1H-imidazol-5-yl)propanoyl]amino]-3-methyl-pentanoyl]amino]butylcarbamoyl]-2-methyl-butyl]amino]-1-(1H-imidazol-5-ylmethyl)-2-oxo-ethyl]benzamide
N-[(1R)-2-[[(1R)-1-[5-[[(2S)-2-[[(2S)-2-benzamido-3-(1H-imidazol-5-yl)propanoyl]amino]-3-methyl-pentanoyl]amino]pentylcarbamoyl]-2-methyl-butyl]amino]-1-(1H-imidazol-5-ylmethyl)-2-oxo-ethyl]benzamide
N-[(1R)-2-[[(1R)-1-[6-[[(2S)-2-[[(2S)-2-

N-[(1R)-2-[[(1R)-1-[8-[[(2S)-2-[[(2S)-2-benzamido-3-(1H-imidazol-5-yl)propanoyl]amino]-3-methyl-pentanoyl]amino]octylcarbamoyl]-2-methyl-butyl]amino]-1-(1H-imidazol-5-ylmethyl)-2-oxo-ethyl]benzamide
N-[(1R)-2-[[(1R)-1-[9-[[(2S)-2-[[(2S)-2-benzamido-3-(1H-imidazol-5-yl)propanoyl]amino]-3-methyl-pentanoyl]amino]nonylcarbamoyl]-2-methyl-butyl]amino]-1-(1H-imidazol-5-ylmethyl)-2-oxo-ethyl]benzamide
N-[(1R)-2-[[(1R)-1-[10-[[(2S)-2-[[(2S)-2-benzamido-3-(1H-imidazol-5-yl)propanoyl]amino]-3-methyl-pentanoyl]amino]decylcarbamoyl]-2-methyl-butyl]amino]-1-(1H-imidazol-5-ylmethyl)-2-oxo-ethyl]benzamide
N-[(1R)-2-[[(1R)-1-[11-[[(2S)-2-[[(2S)-2-benzamido-3-(1H-imidazol-5-yl)propanoyl]amino]-3-methyl-pentanoyl]amino]undecylcarbamoyl]-2-methyl-butyl]amino]-1-(1H-imidazol-5-ylmethyl)-2-oxo-ethyl]benzamide
N-[(1R)-2-[[(1R)-1-[12-[[(2S)-2-[[(2S)-2-

TABLE 3-continued

Non-limiting examples of other pH tuneable amido gellants having structure [I]:

| | |
|---|---|
| benzamido-3-(1H-imidazol-5-yl)propanoyl]amino]-3-methyl-pentanoyl]amino]hexylcarbamoyl]-2-methyl-butyl]amino]-1-(1H-imidazol-5-ylmethyl)-2-oxo-ethyl]benzamide | benzamido-3-(1H-imidazol-5-yl)propanoyl]amino]-3-methyl-pentanoyl]amino]dodecylcarbamoyl]-2-methyl-butyl]amino]-1-(1H-imidazol-5-ylmethyl)-2-oxo-ethyl]benzamide |
| N-[(1R)-2-[[(1R)-1-[7-[[(2S)-2-[[(2S)-2-benzamido-3-(1H-imidazol-5-yl)propanoyl]amino]-3-methyl-pentanoyl]amino]heptylcarbamoyl]-2-methyl-butyl]amino]-1-(1H-imidazol-5-ylmethyl)-2-oxo-ethyl]benzamide | |

TABLE 4

Non-limiting examples of pH tuneable amido gellants having structure [II].

(2S)-2-[[2-(dodecanoylamino)acetyl]amino]propanoic acid

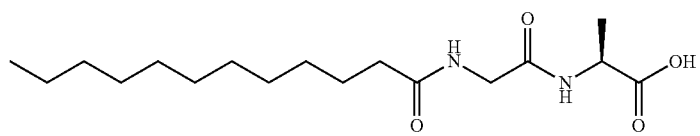

(2S)-2-[[2-[[2-(dodecanoylamino)acetyl]amino]acetyl]amino]propanoic acid

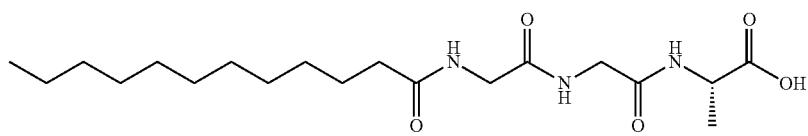

(2S)-2-[[2-(dodecanoylamino)acetyl]amino]-2-phenyl-acetic acid

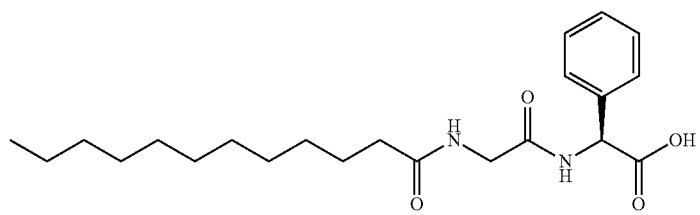

(2S)-2-[[2-(dodecanoylamino)acetyl]amino]-3-methyl-butanoic acid

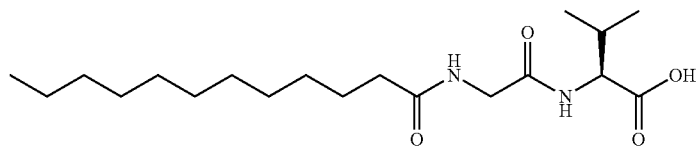

(2S)-2-[[2-(dodecanoylamino)acetyl]amino]acetic acid

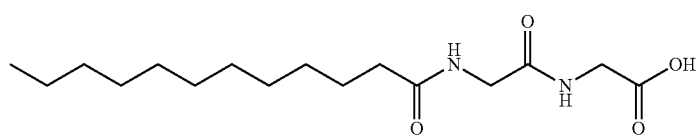

(2S)-2-[[2-(hexadecanoylamino)acetyl]amino]propanoic acid

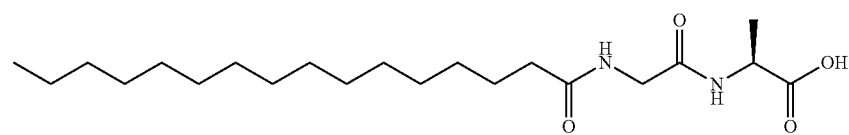

In certain embodiments of both types of pH tunable amido gellant structures, AA comprises at least one of: Alanine; β-Alanine and substituted Alanines; Linear Amino-Alkyl Carboxylic Acid; Cyclic Amino-Alkyl Carboxylic Acid; Aminobenzoic Acid Derivatives; Aminobutyric Acid Derivatives; Arginine and Homologues; Asparagine; Aspartic Acid; p-Benzoyl-Phenylalanine; Biphenylalanine; Citrulline; Cyclopropylalanine; Cyclopentylalanine; Cyclohexylalanine; Cysteine, Cystine and Derivatives; Diaminobutyric Acid Derivatives; Diaminopropionic Acid; Glutamic Acid Derivatives; Glutamine; Glycine; Substituted Glycines; Histidine; Homoserine; Indole Derivatives; Isoleucine; Leucine and Derivatives; Lysine; Methionine; Naphthylalanine; Norleucine; Norvaline; Ornithine; Phenylalanine; Ring-Substituted Phenylalanines; Phenylglycine; Pipecolic Acid, Nipecotic Acid and Isonipecotic Acid; Proline; Hydroxyproline; Thiazolidine; Pyridylalanine; Serine; Statine and Analogues; Threonine; Tetrahydronorharman-3-carboxylic Acid; 1,2,3, 4-Tetrahydroisoquinoline; Tryptophane; Tyrosine; Valine; and combinations thereof.

The pH tunable amido gellant molecule may also comprise protective groups, preferably from 1 to 2 protective groups, preferably two protective groups. Examples of suitable protective groups are provided in "Protecting Groups", P. J. Kocienski, ISBN 313 135601 4, Georg Thieme Verlag, Stuttgart; and "Protective Groups in Organic Chemistry", T. W. Greene, P. G. M. Wuts, ISBN 0-471-62301-6, John Wiley & Sons, Inc, New York.

The pH tunable amido gellant preferably has a minimum gelling concentration (MGC) of from 0.1 to 100 mg/mL in the consumer product composition, at the target pH of the composition, preferably from 0.1 to 25 mg/mL, more preferred from 0.5 to 10 mg/mL in accordance with the MGC Test Method. The MGC as used herein can be represented as mg/ml or as a wt %, where wt % is calculated as the MGC in mg/ml divided by 10. In one embodiment, when measured in the consumer product composition, the MGC is from 0.1 to 100 mg/mL, preferably from 0.1 to 25 mg/mL of said pH tunable amido gellant, more preferably from 0.5 to 10 mg/mL, or at least 0.1 mg/mL, at least 0.3 mg/mL, at least 0.5 mg/mL, at least 1.0 mg/mL, at least 2.0 mg/mL, at least 5.0 mg/mL of pH tunable amido gellant. While consumer product compositions may have a pH tunable amido gellant concentration either above or below the MGC, the pH tunable amido gellants result in particularly useful rheologies below the MGC.

Water and/or Non-Aminofunctional Organic Solvent:

The consumer product composition may be dilute or concentrated aqueous liquids. Alternatively, the consumer product composition may be almost entirely non-aqueous, and comprising a non-aminofunctional organic solvent. Such consumer product compositions may comprise very little water, for instance, that may be introduced with other raw materials. Preferably, the consumer product composition comprises from 1% to 95% by weight of water and/or non-aminofunctional organic solvent. For concentrated detergents, the composition comprises preferably from 5% to 70%, more preferably from 10% to 50%, most preferably from 15% to 45% by weight, water and/or non-aminofunctional organic solvent.

As used herein, "non-aminofunctional organic solvent" refers to any organic solvent which contains no amino functional groups. Preferred non-aminofunctional organic solvents include monohydric alcohols, dihydric alcohols, polyhydric alcohols, glycerol, glycols, polyalkylene glycols such as polyethylene glycol, and mixtures thereof. Highly preferred are mixtures of solvents, especially mixtures of two or more of the following: lower aliphatic alcohols such as ethanol, propanol, butanol, isopropanol; diols such as 1,2-propanediol or 1,3-propanediol; and glycerol. Also preferred are propanediol and mixtures thereof with diethylene glycol where the mixture contains no methanol or ethanol. Thus embodiments of consumer product compositions may include embodiments in which propanediols are used but methanol and ethanol are not used.

Preferable non-aminofunctional organic solvents are liquid at ambient temperature and pressure (i.e. 21° C. and 1 atmosphere), and comprise carbon, hydrogen and oxygen.

Method of Making di-Amido Gellants:

Materials can be bought from his Biotech GmbH, Waldershofer Str. 49-51, 95615 Marktredwitz, Germany; Bachem Holding AG, Hauptstrasse 144, 4416 Bubendorf, Switzerland; Sigma Aldrich NV/SA, Kardinaal Cardijnplein 8, 2880 Bornem, Belgium;

Example Method 1

Synthesis of (2S)-2-[[2-(dodecanoylamino)acetyl]amino]propanoic acid

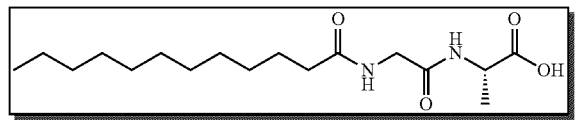

(2S)-2-[[2-(dodecanoylamino)acetyl]amino]propanoic acid is obtained by preparing a first solution by dissolving H-Gly-Ala-OH (30 mmol) in Sodium hydroxide (0.105 M, 300 mL). This first solution is placed in a round bottomed flask with an efficient magnetic stirrer. The flask is completely immersed in an ice bath and during the reaction and the magnetic stirrer is set at 1800 rpm. Lauroyl chloride (9.84 grams, 45 mmol) and sodium hydroxide (3M, 15 mL) are drop wise added to this first solution at the same rate in such a way that the pH of the reaction mixture does not decrease below 10. When the reaction is completed, the suspension is acidified carefully with chloride acid 2M. The residue obtained after filtration (filtering plate n° 3) is extracted with petroleum ether to remove the fatty acid. The resulting white solid is dried under vacuum oven (PSelecta) at 60° C. for 24 h. The yield obtained is 89%.

Example Method 2

Synthesis of (2S)-2-[[2-(hexadecanoylamino)acetyl]amino]propanoic acid

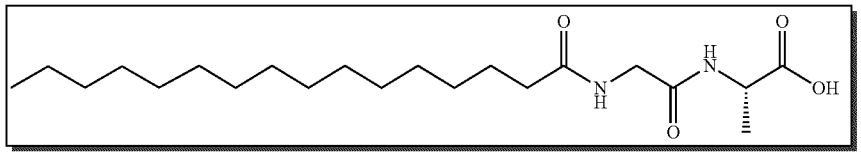

(2S)-2-[[2-(hexadecanoylamino)acetyl]amino]propanoic acid is obtained by preparing a first solution by dissolving Glycyl-L-alanine (30 mmol) in Sodium hydroxide (0.105 M, 300 mL). This first solution is placed in a round bottomed flask with an efficient magnetic stirrer. The flask is completely immersed in an ice bath and during the reaction and the magnetic stirrer is set at 1800 rpm. Palmitoyl chloride (12.37 grams, 45 mmol) and sodium hydroxide (3M, 15 mL) are drop wise added to this first solution at the same rate in such a way that the pH of the reaction mixture does not decrease below 10. When the reaction is completed, the suspension is acidified carefully with chloride acid 2M. The residue obtained after filtration (filtering plate n° 3) is extracted with petroleum ether to remove the fatty acid. The resulting white solid is dried under vacuum oven (PSelecta) at 60° C. for 24 h. The yield obtained is 94%. (2S)-2-[[2-(hexadecanoylamino)acetyl]amino]propanoic acid is characterize using infrared, $^1$H NMR and $^{13}$C NMR obtaining following results:

IR (KBr): 3379, 3290, 2916, 2849, 1728, 1651, 1625, 1537 $cm^{-1}$.

$^1$H NMR (300 MHz, [D6]DMSO, 30° C.): δ 12.33 (s, 1H), 8.03 (d, J=6.8 Hz, 1H), 7.93 (m, 1H), 4.26-4.11 (m, 1H), 3.77-3.59 (m, 2H), 2.13 (dt, J=20.2, 7.0 Hz, 2H), 1.46 (m, 5H), 1.22 (m, 24H), 0.84 (m, 3H) ppm.

$^{13}$CNMR (75 MHz, [D6]DMSO, 30° C.): δ=174.63, 173.16, 169.40, 48.10, 42.31, 35.87, 31.99, 29.76, 29.55, 29.41, 25.87, 22.78, 17.99, 14.56 ppm.

HRMS (ESI–TOF+): calcd. for $C_{21}H_{40}N_2O_4{}^+[M+H]^+$= 385.3066. found 385.3071 (Δ=1.3 ppm).

Test Methods:

1. Turbidity (NTU):

Turbidity (measured in NTU: Nephelometric Turbidity Units) according to the present invention is measured using a Hach 2100P turbidity meter calibrated according to the procedure provided by the manufacture. The sample vials are filled with 15 ml of representative sample and capped and cleaned according to the operating instructions. If necessary, the samples are degassed to remove any bubbles either by applying a vacuum or using an ultrasonic bath (see operating manual for procedure). The turbidity is measured using the automatic range selection.

2. Minimum Gelling Concentration (MGC)

MGC is calculated by a tube inversion method based on R. G. Weiss, P. Terech; "Molecular Gels: Materials with self-assembled fibrillar structures" 2006 springer, p 243. In order to determine the MGC, three screenings are done:

a) First screening: prepare several vials increasing the pH tunable amido gellant concentration from 0.5% to 5.0 weight % in 0.5% steps, at the target pH.

b) Determine in which interval the gel is formed (one inverted sample still flowing and the next one is already a strong gel). In case no gel is formed at 5%, higher concentrations are used.

c) Second screening: prepare several vials increasing the pH tunable amido gellant concentration in 0.1 weight % steps in the interval determined in the first screening, at the target pH.

d) Determine in which interval the gel is formed (one inverted sample still flowing and the next one is already a strong gel)

e) Third screening: in order to have a very precise percentage of the MGC, run a third screening in 0.025 weight % steps in the interval determined in the second screening, at the target pH.

f) The Minimum Gelling Concentration (MGC) is the lowest concentration which forms a gel in the third screening (does not flow on inversion of the sample).

For each screening, samples are prepared and treated as follows: 8 mL vials (Borosilacate glass with Teflon cap, ref. B7857D, Fisher Scientific Bioblock) are filled with 2.0000±0.0005 g (KERN ALJ 120-4 analytical balance with ±0.1 mg precision) of the fluid (comprising the consumer product composition and pH tunable amido gellant) for which we want to determine the MGC. The vial is sealed with the screw cap and left for 10 minutes in an ultrasound bath (Elma Transsonic T 710 DH, 40 kHz, 9.5 L, at 25° C. and operating at 100% power) in order to disperse the solid in the liquid. Complete dissolution is then achieved by heating, using a heating gun (Bosch PHG-2), and gentle mechanical stirring of the vials. It is crucial to observe a completely clear solution. Handle vials with care. While they are manufactured to resist high temperatures, a high solvent pressure may cause the vials to explode. Vials are cooled to 25° C., for 10 min in a thermostatic bath (Compatible Control Thermostats with controller CC2, D77656, Huber). Vials are inverted, left inverted for 1 minute, and then observed for which samples do not flow. After the third screening, the concentration of the sample that does not flow after this time is the MGC. For those skilled in the art, it is obvious that during heating solvent vapours may be formed, and upon cooling down the samples, these vapours can condense on top of the gel. When the vial is inverted, this condensed vapour will flow. This is discounted during the observation period. If no gels are obtained in the concentration interval, higher concentrations must be evaluated.

3. pH Measurement of a Liquid Detergent Composition pH measurement of a liquid detergent composition may be measured using test method EN 1262.

4. Rheology

An AR-G2 rheometer from TA Instruments is used for rheological measurements.

Plate: 40 mm standard steel parallel plate, 300 μm gap.

1. Gel strength: The gel strength is measured using a stress sweep test whereby the oscillation stress is increased from 0.001 Pa to 10 Pa, taking 10 points per decade at 20° C. and at a frequency of 1 Hz. We use G' and G" within the linear viscoelastic region and the oscillation stress at the point where G' and G" cross over as a measure for the gel strength, as shown in FIG. 1.

Figure 2:
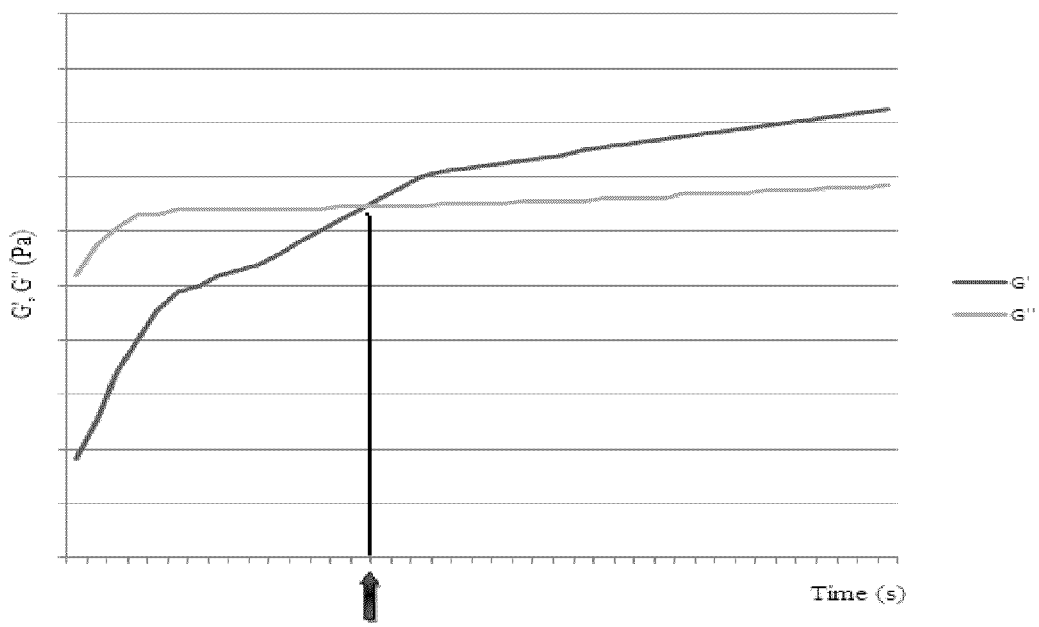
FIG. 2 details G' and G" cross over as a measure of restructuring kinetics.

2. Recovery of structure: first we apply a pre-shear of 30 s−1 at 20° C. for 60 s, after which we follow how the structure recovers applying a time sweep test with an oscillation stress of 0.02 Pa and a single frequency of 1 Hz at 20° C. for 10 minutes. As a measure of the restructuring kinetics, we use G' and G" cross over, as shown in the FIG. 2.

EXAMPLES

Example 1

A Liquid Laundry Detergent Composition is Prepared as Follows

Step 1: A structurant premix A1 is prepared by dissolving 0.20 grams N,N'-(2S,2'S)-1,1'-(hexane-1,6-diylbis(azanediyl))bis(3-methyl-1-oxobutane-2,1-diyl)diisonicotinamide in 12.0 grams of 50% citric acid aqueous solution (prepared by dissolving 6.0 grams of citric acid solid in 6.0 grams deionized water) at 25° C.
Step 2: A detergent feed B1 having the composition described in Table 5 is prepared.

TABLE 5

Composition of detergent feed B1

| Ingredient | Detergent Feed B1 Grams |
|---|---|
| Linear Alkylbenzene sulfonic acid (LAS) | 12.0 |
| C12-14 alkyl ethoxy 3 sulfate Mono Ethanol Amine salt | 9.3 |
| C12-14 alkyl 7-ethoxylate | 8.0 |
| 1,2-propanediol | 9.8 |
| C12-18 Fatty Acid | 10.0 |
| Grease Cleaning Alkoxylated Polyalkylenimine Polymer[1] | 0.9 |
| PEG PVAc Polymer[2] | 0.9 |
| Soil Suspending Alkoxylated Polyalkylenimine Polymer[3] | 2.2 |
| Hydroxyethane diphosphonic acid | 1.6 |
| FWA | 0.23 |
| Ethanol | 1.5 |
| Boric acid | 0.5 |
| MEA | Up to pH 8 |
| Water up to | 66 grams |

[1]600 g/mol molecular weight polyethylenimine core with 24 ethoxylate groups per —NH and 16 propoxylate groups per —NH.
[2]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is 6000 and the weight ratio of the polyethylene oxide to polyvinyl acetate is 40 to 60 and no more than 1 grafting point per 50 ethylene oxide units.
[3]600 g/mol molecular weight polyethylenimine core with 20 ethoxylate groups per —NH.

Step 3: 12.4 grams of structurant premix A1 is mixed with 66 grams of detergent feed B1 at 600 rpm for 10 min, at 25° C., and the resulting mixture is adjusted to pH 8 with MEA.
Step 4: The pH sensitive ingredients (1.5 grams protease, 0.7 grams amylase, 0.1 grams mannanase, 0.1 grams xyloglucanase, 0.4 grams pectate lyase and 1.7 grams of perfume) and deionized water (to bring the final weight up to 100 grams) are added under gentle stirring, at 500-600 rpm for 10 min.

Example 2

Unit Dose Laundry Detergent

A laundry unit dose comprising the fluid detergent composition is prepared as follows:
Step 1: A structurant premix A2 is prepared by fully dissolving 0.20 grams N,N'-(2S,2'S)-1,1'-(octane-1,8-diylbis(azanediyl))bis(3-methyl-1-oxobutane-2,1-diyl)diisonicotinamide in 1.0 grams of citric acid and 3 grams of deionized water at 25° C.
Step 2: A detergent feed B2 having the composition described in Table 6 is prepared.

TABLE 6

Composition of detergent feed B2

| Ingredient | Detergent Feed B2 % of base @100% active |
|---|---|
| 1,2-Propanediol | 15 |
| MEA | 10 |
| Glycerol | 5 |
| Hydroxyethane diphosphonic acid | 1 |
| Potassium sulfite | 0.2 |
| C12-45 alkyl 7-ethoxylate | 20 |
| Linear Alkylbenzene sulfonic acid | 24.5 |
| FWA | 0.2 |
| C12-18 Fatty Acid | 16 |
| Ethoxysulfated Hexamethylene Diamine Dimethyl Quat | 2.9 |
| Soil Suspending Alkoxylated Polyalkylenimine Polymer[3] | 1 |
| MgCl$_2$ | 0.2 |
| Water and minors | Up to 100% |

Step 3: 4.2 grams of structurant premix A2 are mixed with 34.5 grams of detergent feed B2 at 600 rpm for 10 min, at 25° C., for 5 minutes. The resulting mixture is adjusted to pH 8 with MEA and pH sensitive ingredients listed in Table 7 are added at 600 rpm, 25° C., and mixed for 2 minutes:

TABLE 7 pH sensitive ingredients.

| Ingredient | % of base @100% active |
|---|---|
| Protease enzyme | 1.4 |
| Mannanase enzyme | 0.1 |
| Amylase enzyme | 0.2 |

The fluid detergent composition is then packed into a polyvinyl alcohol pouch.

Examples 3A to 3E

Fluid Detergent Fabric Care Compositions Comprising Amido-Gellants

Step 1: A structurant premix A3 is prepared by dissolving 5 grams N,N'-(2S,2'S)-1,1'-(dodecane-1,12-diylbis(azanediyl))bis(3-methyl-1-oxobutane-2,1-diyl)diisonicotinamide in 95 grams of 25% sulfuric acid aqueous solution (Sigma-Aldrich) at 25° C.
Step 2: A detergent feed B3A to B3E having the composition described in Table 8 is prepared.

TABLE 8

Composition of detergent feed B3A to B3E

| Ingredient | B3A Wt % | B3B Wt % | B3C Wt % | B3D Wt % | B3E Wt % |
|---|---|---|---|---|---|
| C12-15 alkyl polyethoxylate (3.0) sulfate | 6.7 | 6.5 | 7.8 | 6.4 | 5.7 |
| C11.8 linear alkylbenzene sulfonc acid | 19.4 | 18.9 | 19.0 | 14.6 | 16.4 |
| C14-15 alkyl 7-ethoxylate | 11.8 | 11.5 | 3.9 | 4.8 | 16.4 |
| C12-14 alkyl 7-ethoxylate | — | 0.9 | 1.0 | 1.1 | 0.9 |
| 1,2 Propane diol | 7.0 | 5.2 | 8.2 | 9.1 | 6.9 |
| Ethanol | 1.8 | 1.7 | 2.0 | 2.3 | 1.7 |
| Di Ethylene Glycol | — | 3.4 | — | — | — |
| Na Cumene Sulfonate | 5.3 | 5.2 | 6.1 | 6.8 | 5.2 |
| C12-18 Fatty Acid | 4.6 | 4.5 | 6.7 | 5.9 | 4.5 |
| Citric acid | 4.6 | 4.5 | 7.6 | 9.8 | 4.5 |
| Fluorescent Whitening Agent | 0.18 | — | 0.20 | 0.23 | 0.17 |
| Diethylene Triamine Penta Acetic acid | — | 0.860 | — | — | — |
| Diethylene Triamine Penta Methylene Phosphonic acid | 0.53 | 0.17 | 0.61 | 0.68 | 0.52 |
| Soil Suspending Alkoxylated Polyalkylenimine Polymer[1] | 1.4 | 0.9 | — | — | 1.4 |
| Zwitterionic ethoxylated quaternized sulfated hexamethylene diamine[2] | 1.8 | 1.7 | 1.8 | 2.3 | 1.7 |
| Grease Cleaning Alkoxylated Polyalkylenimine Polymer[3] | 0.7 | 0.7 | — | 0.5 | — |
| PEG-PVAc Polymer[4] | — | 0.9 | — | — | — |
| Monoethanolamine Borate | 3.5 | 1.7 | 4.1 | 4.6 | 3.4 |
| 4-Formyl Phenyl Boronic Acid | — | 0.05 | — | — | — |
| Sodium formate | 0.7 | 0.7 | 0.8 | 0.9 | 0.7 |
| Calcium chloride | 0.09 | 0.09 | 0.10 | 0.11 | 0.09 |
| Acticide MBS 2550 | 0.010 | 0.010 | 0.010 | 0.010 | 0.010 |
| Water | up to 100% | up to 100% | up to 100% | up to 100% | up to 100% |

[1]600 g/mol molecular weight polyethylenimine core with 20 ethoxylate groups per —NH. Available from BASF (Ludwigshafen, Germany)
[2]Described in WO 01/05874 and available from BASF (Ludwigshafen, Germany)
[3]600 g/mol molecular weight polyethylenimine core with 24 ethoxylate groups per —NH and 16 propoxylate groups per —NH. Available from BASF (Ludwigshafen, Germany).
[4]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).

Step 3: Structurant premix A3 (amounts listed in Table 9) is mixed with 70 grams of detergent feeds B3A to B3E at 400 rpm for 10 min, at 35° C.

TABLE 9 addition of premix A3

| Ingredient | 3A grams | 3B grams | 3C grams | 3D grams | 3E grams |
|---|---|---|---|---|---|
| Premix A3 | 5 | 3 | 4 | 6 | 3.6 |

The resulting mixture is adjusted to pH 8 with sodium hydroxide 20% and pH sensitive ingredients listed in Table 10 are added at 600 rpm, 25° C., and mixed for 5 minutes.

TABLE 10 pH sensitive ingredients.

| Ingredient | 3A Wt % | 3B Wt % | 3C Wt % | 3D Wt % | 3E Wt % |
|---|---|---|---|---|---|
| Protease (40.6 mg/g)[1] | 0.5 | 0.5 | 0.5 | 0.5 | 0.5 |
| Natalase 200L (29.26 mg/g)[2] | 0.1 | 0.1 | 0.1 | 0.1 | 0.1 |
| Termamyl Ultra (25.1 mg/g) | 0.05 | 0.05 | 0.05 | 0.05 | 0.05 |
| Mannaway 25L (25 mg/g)[2] | 0.05 | 0.05 | 0.05 | 0.05 | 0.05 |
| Lipase (16.91 mg/g)[2] | 0.5 | — | 0.25 | — | 0.5 |
| Lipolex ®[2] | — | 0.2 | — | — | — |
| Lipex ®[2] | — | — | — | 0.25 | — |
| Whitezyme (20 mg/g)[2] | 0.05 | 0.05 | 0.05 | 0.05 | 0.05 |
| Perfume Microcapsules[3] | — | — | — | 0.2 | — |
| Mica | — | — | — | — | 0.05 |
| Silicone suds suppressor | — | 0.1 | — | — | — |
| Water, perfumes, dyes, neutralizers, and other optional components (pH to 8.0-8.2) | to 100% | to 100% | to 100% | to 100% | to 100% |

[1]Available from Genencor International, South San Francisco, CA.
[2]Available from Novozymes, Denmark.
[3]Perfume microcapsules can be prepared as follows: 25 grams of butyl acrylate-acrylic acid copolymer emulsifier (Colloid C351, 25% solids, pka 4.5-4.7, Kemira Chemicals, Inc. Kennesaw, Georgia U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, Cytec Industries West Paterson, New Jersey, U.S.A.) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Missouri, U.S.A.) is added to the suspension.

Examples 4A to 4S

Hand-Dish Washing Fluid Detergent Compositions Comprising Amido-Gellants

Hand-dish washing liquid detergent compositions may be prepared by mixing together the ingredients listed in the proportions shown:

TABLE 11

Hand-dish washing fluid detergent compositions comprising amido-gellants

| | Ex 4A | Ex 4B | Ex 4C | Ex 4D | Ex 4E | Ex 4F |
|---|---|---|---|---|---|---|
| Alkyl Ethoxy Sulfate AE0.6S | 22.0 | 19.0 | 27.0 | 20.0 | 22.0 | 22.0 |
| Linear C12-C14 Amine oxide | 6.0 | 4.5 | — | — | 6.0 | 5.0 |
| C9-C11 alkyl EO8 ethoxylate | 7.0 | — | — | — | — | — |
| L-Glutamic acid-N,N-di(acetic acid) tetrasodium salt | 1.0 | — | — | 0.1 | — | — |
| Sodium Citrate | — | 1.0 | — | 0.5 | 0.8 | — |
| Solvent: ethanol, isopropylalcohol, ... | 2.5 | 4.0 | 3.0 | 2.0 | 3.0 | 2.5 |
| Polypropylene glycol Mw2000 | 1.0 | 0.5 | 1.0 | — | 2.0 | 1.0 |
| Sodium Chloride | 0.5 | 1.0 | 1.0 | 0.5 | 0.5 | 0.5 |
| N,N'-(2S,2'S)-1,1'-(dodecane-1,12-diylbis(azanediyl))bis(3-methyl-1-oxobutane-2,1-diyl)diisonicotinamide | 0.05 | 0.20 | 0.10 | 0.15 | 0.25 | 0.20 |

Minors and Balance with water up to 100%

TABLE 12

Hand-dish washing fluid detergent compositions comprising amido-gellants

| | Ex 4G | Ex 4H | Ex 4I | Ex 4J |
|---|---|---|---|---|
| Alkyl Ethoxy Sulfate AE1.0S | 13 | 16 | 17 | 20 |
| C12-C14 Amine oxide | 4.5 | 5.5 | 4.0 | 4.5 |
| C9-C11 alkyl EO8 ethoxylate | 4 | 4 | — | — |
| L-Glutamic acid-N,N-di(acetic acid) tetrasodium salt | 0.7 | — | — | — |
| Sodium Citrate | — | — | 0.2 | — |
| Solvent: ethanol, isopropylalcohol, ... | 2.0 | 2.0 | 2.0 | 1.5 |
| Polypropylene glycol Mw2000 | 0.5 | 0.3 | 0.5 | 0.8 |
| Sodium Chloride | 0.5 | 0.8 | 0.4 | 0.5 |
| N,N'-(2S,2'S)-1,1'-(dodecane-1,12-diylbis(azanediyl))bis(3-methyl-1-oxobutane-2,1-diyl)diisonicotinamide | 0.30 | 0.20 | 0.50 | 0.25 |

Minors and Balance with water up to 100%

TABLE 13

Hand-dish washing fluid detergent compositions comprising amido-gellants

| | Ex 4K | Ex 4L | Ex 4M | Ex 4N | Ex 4O |
|---|---|---|---|---|---|
| Linear Alkylbenzene Sulfonate | 21.0 | 21.0 | 12.0 | 13.0 | — |
| Alkyl Ethoxy Sulfate AE1.0S | — | — | 14.0 | 5.0 | 17.0 |
| C12-14 alpha olefin sulfonate | — | — | — | — | 6.0 |
| Coco amido propyl Amine Oxide | — | — | — | 1.0 | 5.0 |
| alkylpolyglucoside | — | 2.0 | — | — | — |
| C9-C11 alkyl EO8 ethoxylate | 5.0 | 4.0 | 8.0 | 4.0 | 3.0 |
| L-Glutamic acid-N,N-di(acetic acid) tetrasodium salt | 0.5 | — | — | — | — |
| N,N'-(2S,2'S)-1,1'-(dodecane-1,12-diylbis(azanediyl))bis(3-methyl-1-oxobutane-2,1-diyl)diisonicotinamide | 0.15 | 0.15 | 0.10 | 0.20 | 0.10 |

Minors and Balance with water up to 100%

TABLE 14

Hand-dish washing fluid detergent compositions comprising amido-gellants

| | Ex 4P | Ex 4Q | Ex 4R | Ex 4S |
|---|---|---|---|---|
| Alkyl Ethoxy Sulfate AE2.0S | 17.0 | 12.0 | 24.0 | 29.0 |
| C12-14 alpha olefin sulfonate | — | — | 1.0 | — |
| Paraffin Sulfonate (C15) | 9.0 | 1.0 | 1.0 | — |
| Coco amido propyl amine oxide | — | 6.0 | — | 1.0 |
| C12-C14 Akylpolyglucoside | — | 3.0 | 2.0 | — |
| C9-C11 alkyl EO8 ethoxylate | 8.0 | 2.0 | — | — |
| L-Glutamic acid-N,N-di(acetic acid) tetrasodium salt | 0.5 | — | 0.5 | — |
| Polypropylene glycol MW2000 | 1.0 | 1.0 | — | 0.5 |
| N,N'-(2S,2'S)-1,1-(dodecane-1,12-diylbis(azanediyl))bis(3-methyl-1-oxobutane-2,1-diyl)diisonicotinamide | 0.10 | 0.25 | 0.10 | 0.15 |

Minors and Balance with water up to 100%

N,N'-(2S,2'S)-1,1'-(dodecane-1,12-diylbis(azanediyl))bis(3-methyl-1-oxobutane-2,1-diyl)diisonicotinamide has been added as Premix A3 prepared in example 3. Afterwards, pH was adjusted with 20% sodium hydroxide aqueous solution to pH 9 (for examples 4A to 4J) and pH 8 (examples 4K to 4S).

Examples 5A, 5B and 5C

Compacted Laundry Fluid Detergent Compositions (25 mL Dosage) Comprising Amido-Gellants Step 1: A structurant premix A5 is prepared by dissolving 10 grams N,N'-(2S,2'S)-1,1'-(dodecane-1,12-diylbis(azanediyl))bis(3-methyl-1-oxobutane-2,1-diyl)diisonicotinamide in 90 grams 20% $C_{11-8}$ HLAS in 1,2-propanediol solution (prepared by adding 20 grams $C_{11-8}$ HLAS to 80 grams 1,2-propanediol at 50° C.) at 45° C.

Step 2: Detergent feeds B5A and B5B having the composition described in Table 15 are prepared.

TABLE 15

Composition of detergent feeds B5A, B5B, B5C

| Ingredients | 5A | 5B | 5C |
|---|---|---|---|
| | Weight % | | |
| Monoethanolamine: $C_{12-15}$ EO•3•$SO_3$H | 40.5 | 43.3 | 41.5 |
| Monoethanolamine: $C_{16-17}$ highly soluble alkyl sulfate | 6.5 | 7.4 | 7.0 |
| $C_{12-14}$ dimethylamine-N-oxide | 1.9 | 2.1 | 2.0 |
| Ethoxylated Polyethyleneimine[1] | 4.3 | 4.9 | 4.3 |
| Citric acid | — | 2.5 | 1.0 |
| Amphiphilic alkoxylated grease cleaning polymer[2] | 4.3 | 3.1 | 4.3 |
| $C_{12-18}$ Fatty acid | 3.3 | — | 3.3 |
| Suds suppression polymer | 0.1 | 0.1 | 0.1 |
| $C_{11-8}$ HLAS | 14.7 | 12.4 | 13.0 |
| Hydroxy Ethylidene 1,1 Di Phosphonic acid | — | 1.2 | — |
| Tiron | 2.2 | — | 2.2 |
| Brightener | 0.1 | 0.2 | 0.1 |
| Water | 5.1 | 6.2 | 4.8 |
| Minors (antioxidant, sulfite, aesthetics, . . .) | 1.6 | 1.9 | 2.0 |
| Buffers (monoethanolamine) | To pH 8.0 | | |
| Solvents (1,2 propanediol, ethanol) | To 100 parts | | |

[1]Polyethyleneimine (MW = 600 grams/mol) with 20 ethoxylate groups per —NH (BASF, Germany)
[2]PG617 or PG640 (BASF, Germany)

Step 3: Structurant premix A5 (amounts listed in Table 16) are mixed with detergent feeds B5A and B5B at 500 rpm for 10 min, at 45° C., for 5 minutes, then, product is cooled to 35° C. and pH is adjusted to 8 with monoethanolamine. Then, product is cooled to 25° C. and perfume and/or perfume microcapsules are added according to table 16.

TABLE 16 addition of premix A5 and formula finishing

| Ingredients | 5A | 5B | 5C |
|---|---|---|---|
| | Weight % | | |
| Detergent feed | 75 | 75 | 75 |
| Premix A5 | 2.5 | 3.0 | 6.0 |
| Monoethanolamine | To pH 8.0 | | |
| Perfume | 1.5 | 1.7 | 1.3 |
| Perfume microcapsules[1] | 2.3 | — | 1.5 |

TABLE 16-continued addition of premix A5 and formula finishing

| Ingredients | 5A | 5B | 5C |
|---|---|---|---|
| | Weight % | | |
| Solvents (1,2 propanediol) | To 100 parts | | |

[1]as described in example 3

Examples 6A and 6B

Laundry Fluid Detergent Composition Comprising Amido-Gellants

Detergent feeds 6A and 6B, having the compositions described in Table 17, are prepared. Then A3 premix is added and pH is adjusted to 8 with sodium hydroxide 20%.

TABLE 17 laundry fluid detergent composition comprising amido-gellants

| Ingredient | 6A Wt % | 6B Wt % |
|---|---|---|
| C12-14 alkyl polyethoxylate (3.0) sulfate | 3.8 | 3.5 |
| $C_{11-8}$ HLAS | 3.7 | 4.0 |
| C12-14 alkyl 7-ethoxylate | 1.4 | 1.4 |
| 1,2 Propane diol | 0.18 | 0.25 |
| Glycerine | 2.00 | 2.00 |
| Diethylene triamine penta acetate | 0.48 | 0.48 |
| Phenoxyethanol | 0.1 | 0.1 |
| Citric acid | 1.70 | 2.5 |
| Fluorescent Whitening Agent | 0.057 | — |
| Dodecyldimethylamine N-oxide | 0.4 | 0.4 |
| Zwitterionic ethoxylated quaternized sulfated hexamethylene diamine[1] | 0.25 | 0.25 |
| Perfume | 0.43 | 0.30 |
| PEG-PVAc Polymer[2] | 0.5 | 0.5 |
| Silicone suds supressor | 0.0025 | 0.0025 |
| Boric Acid | 1.20 | 1.20 |
| Calcium chloride | 0.06 | 0.06 |
| Acticide MBS 2550 | 0.01 | 0.01 |
| Premix A3 | 5.0 | 10.0 |
| Sodium hydroxide 20% | To pH 8 | To pH 8 |
| Water | up to 100% | up to 100% |

[1]Described in WO 01/05874 and available from BASF (Ludwigshafen, Germany)
[2]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is 6000 and the weight ratio of the polyethylene oxide to polyvinyl acetate is 40 to 60 and no more than 1 grafting point per 50 ethylene oxide units.

Example 7

Hand-Dish Washing Fluid Detergent Compositions Comprising Amido-Gellant

Hand-dish washing liquid detergent compositions may be prepared by mixing together the ingredients listed in the proportions shown:

TABLE 18

Hand-dish washing fluid detergent compositions comprising amido-gellant

| | 7 |
|---|---|
| Alkyl Ethoxy Sulfate AE2.0S | 18.0 |
| Coco amido propyl Betaine | 5.0 |
| Polypropylene glycol MW2000 | 0.5 |

TABLE 18-continued

Hand-dish washing fluid detergent compositions comprising amido-gellant

|   | 7 |
|---|---|
| N,N'-(2S,2'S)-1,1'-(octane-1,8-diylbis(azanediyl))bis(3-methyl-1-oxobutane-2,1-diyl)bis(4-hydroxybenzamide) | 0.25 |

Minors, citric acid and Balance with water up to 100% and pH 5.5.

Example 8

A Liquid Laundry Detergent Composition is Prepared as Follows

Step 1: A structurant premix A1 is prepared by dissolving 0.20 grams N,N'-(2S,2'S)-1,1'-(dodecane-1,12-diylbis(azanediyl))bis(3-methyl-1-oxobutane-2,1-diyl)diisonicotinamide in 12.0 grams of 50% citric acid aqueous solution (prepared by dissolving 6.0 grams of citric acid solid in 6.0 grams deionized water) at 25° C.

Step 2: A detergent feed B1 having the composition described in Table 19 is prepared.

TABLE 19

Composition of detergent feed B1

| Ingredient | Detergent Feed B1 Grams |
|---|---|
| Linear Alkylbenzene sulfonic acid (LAS) | 12.0 |
| C12-14 alkyl ethoxy 3 sulfate Mono Ethanol Amine salt | 9.3 |
| C12-14 alkyl 7-ethoxylate | 8.0 |
| 1,2-propanediol | 9.8 |
| C12-18 Fatty Acid | 10.0 |
| Grease Cleaning Alkoxylated Polyalkylenimine Polymer[1] | 0.9 |
| PEG PVAc Polymer[2] | 0.9 |
| Soil Suspending Alkoxylated Polyalkylenimine Polymer[3] | 2.2 |
| Hydroxyethane diphosphonic acid | 1.6 |
| FWA | 0.23 |
| Ethanol | 1.5 |
| Boric acid | 0.5 |
| MEA | Up to pH 8 |
| Water up to | 66 grams |

[1] 600 g/mol molecular weight polyethylenimine core with 24 ethoxylate groups per —NH and 16 propoxylate groups per —NH.
[2] PEG-PVA graft copolymer is a polyvinyl acetate grafted polyethylene oxide copolymer having a polyethylene oxide backbone and multiple polyvinyl acetate side chains. The molecular weight of the polyethylene oxide backbone is 6000 and the weight ratio of the polyethylene oxide to polyvinyl acetate is 40 to 60 and no more than 1 grafting point per 50 ethylene oxide units.
[3] 600 g/mol molecular weight polyethylenimine core with 20 ethoxylate groups per —NH.

Step 3: 12.4 grams of structurant premix A1 is mixed with 66 grams of detergent feed B1 at 600 rpm for 10 min, at 25° C., and the resulting mixture is adjusted to pH 8 with MEA.

Step 4: The pH sensitive ingredients (1.5 grams protease, 0.7 grams amylase, 0.1 grams mannanase, 0.1 grams xyloglucanase, 0.4 grams pectate lyase and 1.7 grams of perfume) and deionized water (to bring the final weight up to 100 grams) are added under gentle stirring, at 500-600 rpm for 10 min

Rheology Data

| | Gel strength | | | |
|---|---|---|---|---|
| Example n. | G' (Pa) | G" (Pa) | Oscillation stress (Pa) | Recovery Time (s) |
| 1 | 90 | 27 | 6.3 | <6 |
| 5A | 70 | 40 | 6.3 | 52 |
| 5C | 8140 | 1540 | >10 | <6 |
| 6A | 60 | 25 | 1.3 | <6 |
| 6B | 3030 | 730 | 8 | <6 |
| 8 | 45 | 5 | >10 | <6 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pH tunable amido-gellant having a formula:

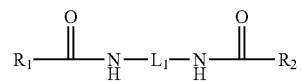

wherein:

at least one of $L_1$, $R_1$ or $R_2$ comprises a pH-sensitive group;

$L_1$ is a backbone moiety having molecular weight from 14 to 500 g/mol; and $R_1$ is $R_3$ or

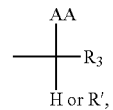

$R_2$ is $R_4$ or
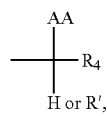
wherein each AA is independently selected from the group consisting of:
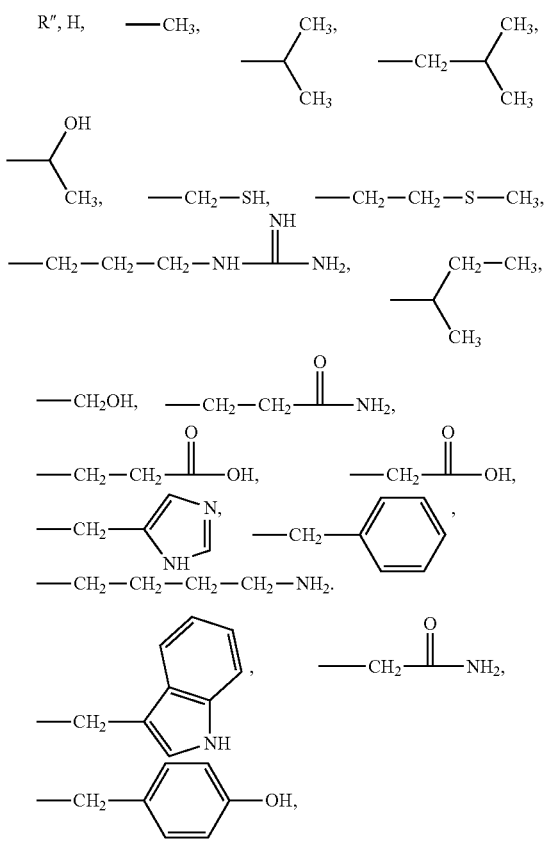
and $R_3$ and $R_4$ independently have the formula:
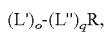
wherein: (o+q) is from 1 to 10; L' and L" are independently selected from the group consisting of:
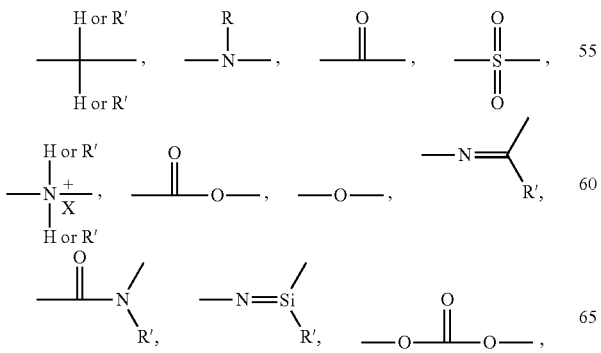
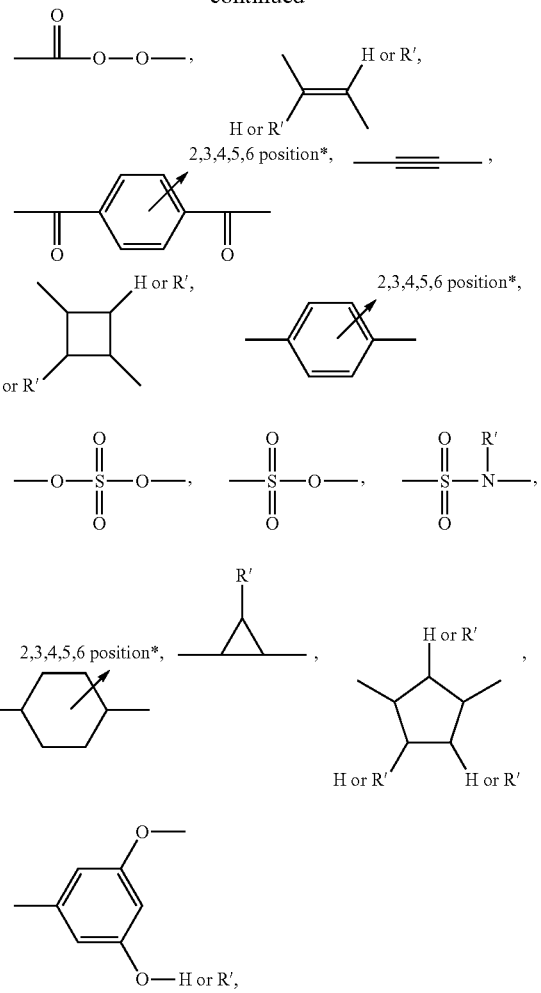
and R, R' and R" are independently selected either from pH-sensitive-groups consisting of:
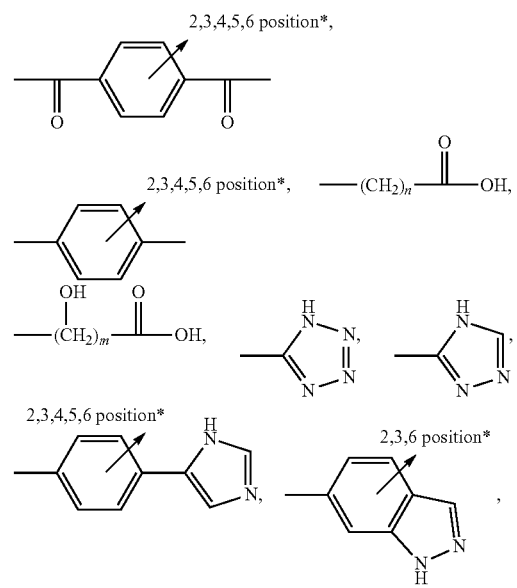

—COOH,

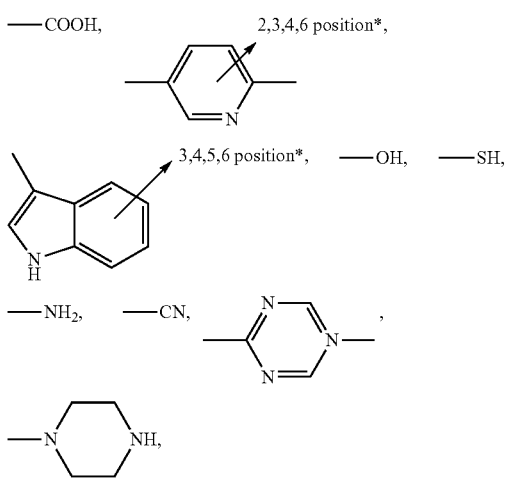

—NH₂, —CN, wherein n and m are integers from 1 to 20;
or from non-pH-sensitive groups consisting of:

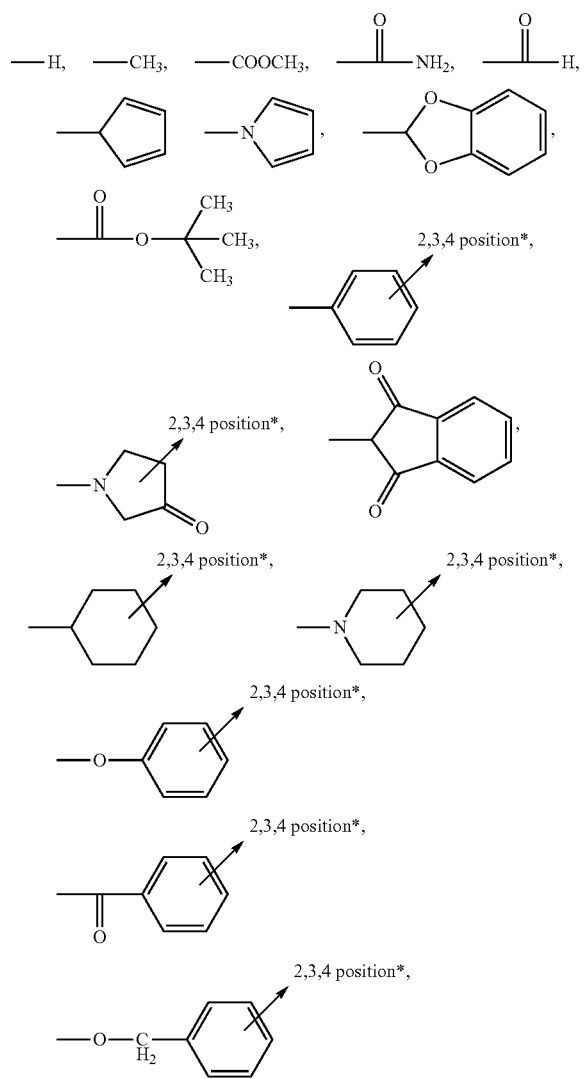

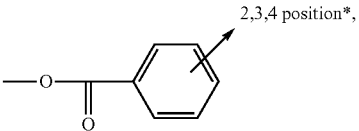

such that at least one of R, R' and R" comprises a pH-sensitive group;
wherein the pH tunable amido-gellant has a pKa of from 1 to 30, and with the exclusion that the di-amido gellant is not a protein.

2. The pH tunable amido-gellant of claim 1, wherein the pH tunable amido-gellant has a pKa of from 1.5 to 14.

3. The pH tunable amido-gellant of claim 1, wherein the pH tunable amido-gellant has a molecular weight from 150 to 1500 g/mol.

4. The pH tunable amido-gellant of claim 1, wherein the pH tunable amido-gellant has a minimum gelling concentration (MGC) of from 0.1 to 100 mg/mL, at the pH of the composition.

5. The pH tunable amido-gellant of claim 1, wherein the pH tunable amido gellant is selected from the group consisting of: N,N'-(2S,2'S)-1,1'-(ethane-1,2-diylbis(azanediyl))bis(3-methyl-1-oxobutane-2,1-diyl)diisonicotinamide; N,N-(2S,2'S)-1,1'-(propane-1,3-diylbis(azanediyl))bis(3-methyl-1-oxobutane-2,1-diyl)diisonicotinamide; N,N-(2S,2'S)-1,1'-(butane-1,4-diylbis(azanediyl))bis(3-methyl-1-oxobutane-2,1-diyl)diisonicotinamide; N,N-(2S,2'S)-1,1'-(pentane-1,5-diylbis(azanediyl))bis(3-methyl-1-oxobutane-2,1-diyl)diisonicotinamide; N,N-(2S,2'S)-1,1'-(hexane-1,6-diylbis(azanediyl))bis(3-methyl-1-oxobutane-2,1-diyl)diisonicotinamide; N,N-(2S,2'S)-1,1'-(heptane-1,7-diylbis(azanediyl))bis(3-methyl-1-oxobutane-2,1-diyl)diisonicotinamide; N,N-(2S,2'S)-1,1'-(octane-1,8-diylbis(azanediyl))bis(3-methyl-1-oxobutane-2,1-diyl)diisonicotinamide; (6S,13S')-6,13-diisopropyl-4,7,12,15-tetraoxo-5,8,11,14-tetraazaoctadecane-1,18-dioic acid; (6S,14S')-6,14-diisopropyl-4,7,13,16-tetraoxo-5,8,12,15-tetraazanonadecane-1,19-dioic acid; (6S,15S')-6,15-diisopropyl-4,7,14,17-tetraoxo-5,8,13,16-tetraazaeicosane-1,20-dioic acid; (6S,16S')-6,16-diisopropyl-4,7,15,18-tetraoxo-5,8,14,17-tetraazaheneicosane-1,2'-dioic acid; (6S,17S')-6,17-diisopropyl-4,7,16,19-tetraoxo-5,8,15,18-tetraazadocosane-1,22-dioic acid; 18S')-6,18-diisopropyl-4,7,17,20-tetraoxo-5,8,16,19-tetraazatricosane-1,23-dioic acid; (6S,19S')-6,19-diisopropyl-4,7,18,21-tetraoxo-5,8,17,20-tetraazatetracosane-1,24-dioic acid; (6S,20S')-6,20-diisopropyl-4,7,19,22-tetraoxo-5,8,18,21-tetraazapentacosane-1,25-dioic acid; (6S,21S')-6,21-diisopropyl-4,7,20,23-tetraoxo-5,8,19,22-tetraazahexacosane-1,26-dioic acid; (6S,22S')-6,22-diisopropyl-4,7,21,24-tetraoxo-5,8,20,23-tetraazaheptacosane-1,27-dioic acid; (6S,23S')-6,23-diisopropyl-4,7,22,25-tetraoxo-5,8,21,24-tetraazaoctacosane-1,28-dioic acid; N,N'-(2S,2'S)-1,1'-(ethane-1,2-diylbis(azanediyl))bis(3-methyl-1-oxobutane-2,1-diyl)bis(4-(1H-imidazol-5-yl)benzamide); N,N'-(2S,2'S)-1,1'-(propane-1,3-diylbis(azanediyl))bis(3-methyl-1-oxobutane-2,1-diyl)bis(4-(1H-imidazol-5-yl)benzamide N,N'-(2S,2'S)-1,1'-(butane-1,4-diylbis(azanediyl))bis(3-methyl-1-oxobutane-2,1-diyl)bis(4-(1H-imidazol-5-yl)benzamide); N,N'-(2S,2'S)-1,1'-(pentane-1,5-diylbis(azanediyl))bis(3-methyl-1-oxobutane-2,1-diyl)bis(4-(1H-imidazol-5-yl)benzamide); N,N'-(2S,2'S)-1,1'-(hexane-1,6-diylbis(azanediyl))bis(3-methyl-1-oxobutane-2,1-diyl)bis(4-(1H-imidazol-5-yl)benzamide); N,N'-(2S,2'S)-1,1'-(heptane-1,7- diylbis(azanediyl))bis(3-methyl-1-oxobutane-2,1-diyl)bis (4-(1H-imidazol-5-yl)benzamide); N,N'-(2S,2'S)-1,1'-(octane-1,8-diylbis(azanediyl))bis(3-methyl-1-oxobutane-2,1-diyl)bis(4-(1H-imidazol-5-yl)benzamide); N,N'-(2S,2'S)-1,1'-(nonane-1,9-diylbis(azanediyl))bis(3-methyl-1-oxobutane-2,1-diyl)bis(4-(1H-imidazol-5-yl)benzamide); N,N'-(2S,2'S)-1,1'-(decane-1,10-diylbis(azanediyl))bis(3-methyl-1-oxobutane-2,1-diyl)bis(4-(1H-imidazol-5-yl)benzamide); N,N'-(2S,2'S)-1,1'-(undecane-1,1'-diylbis(azanediyl))bis(3-methyl-1-oxobutane-2,1-diyl)bis(4-(1H-imidazol-5-yl)benzamide); N,N'-(2S,2'S)-1,1'-(dodecane-1,12-diylbis(azanediyl))bis(3-methyl-1-oxobutane-2,1-diyl)bis(4-(1H-imidazol-5-yl)benzamide); N,N'-(2S,2'S)-1,1'-(nonane-1,9-diylbis(azanediyl))bis(3-methyl-1-oxobutane-2,1-diyl)diisonicotinamide; N,N'-(2S,2'S)-1,1'-(decane-1,10-diylbis(azanediyl))bis(3-methyl-1-oxobutane-2,1-diyl)diisonicotinamide; N,N'-(2S,2'S)-1,1'-(undecane-1,11-diylbis(azanediyl))bis(3-methyl-1-oxobutane-2,1-diyl)diisonicotinamide; N,N'-(2S,2'S)-1,1'-(dodecane-1,12-diylbis(azanediyl))bis(3-methyl-1-oxobutane-2,1-diyl)diisonicotinamide; N,N'-(2S,2'S)-1,1'-(tridecane-1,13-diylbis(azanediyl))bis(3-methyl-1-oxobutane-2,1-diyl)diisonicotinamide; N,N'-(2S,2'S)-1,1'-(tetradecane-1,14-diylbis(azanediyl))bis(3-methyl-1-oxobutane-2,1-diyl)diisonicotinamide; N,N'-(2S,2'S)-1,1'-(hexadecane-1,16-diylbis(azanediyl))bis(3-methyl-1-oxobutane-2,1-diyl)diisonicotinamide; N,N'-(2S,2'S)-1,1'-(octadecane-1,18-diylbis(azanediyl))bis(3-methyl-1-oxobutane-2,1-diyl)diisonicotinamide; N,N'-(2S,2'S)-1,1'-(ethane-1,2-diylbis(azanediyl))bis(1-oxopropane-2,1-diyl)diisonicotinamide; N,N'-(2S,2'S)-1,1'-(propane-1,3-diylbis(azanediyl))bis(1-oxopropane-2,1-diyl)diisonicotinamide; N,N'-(2S,2'S)-1,1'-(butane-1,4-diylbis(azanediyl))bis(1-oxopropane-2,1-diyl)diisonicotinamide; N,N'-(2S,2'S)-1,1'-(pentane-1,5-diylbis(azanediyl))bis(1-oxopropane-2,1-diyl)diisonicotinamide; N,N'-(2S,2'S)-1,1'-(hexane-1,6-diylbis(azanediyl))bis(1-oxopropane-2,1-diyl)diisonicotinamide; N,N'-(2S,2'S)-1,1'-(heptane-1,7-diylbis(azanediyl))bis(1-oxopropane-2,1-diyl)diisonicotinamide; N,N'-(2S,2'S)-1,1'-(octane-1,8-diylbis(azanediyl))bis(1-oxopropane-2,1-diyl)diisonicotinamide; N,N'-(2S,2'S)-1,1'-(nonane-1,9-diylbis(azanediyl))bis(1-oxopropane-2,1-diyl)diisonicotinamide; N,N'-(2S,2'S)-1,1'-(decane-1,10-diylbis(azanediyl))bis(1-oxopropane-2,1-diyl)diisonicotinamide; N,N'-(2S,2'S)-1,1'-(undecane-1,11-diylbis(azanediyl))bis(1-oxopropane-2,1-diyl)diisonicotinamide; N,N'-(2S,2'S)-1,1'-(dodecane-1,12-diylbis(azanediyl))bis(1-oxopropane-2,1-diyl)diisonicotinamide; N,N'-(2S,2'S)-1,1'-(tridecane-1,13-diylbis(azanediyl))bis(1-oxopropane-2,1-diyl)diisonicotinamide; N,N'-(2S,2'S)-1,1'-(tetradecane-1,14-diylbis(azanediyl))bis(1-oxopropane-2,1-diyl)diisonicotinamide; N,N'-(2S,2'S)-1,1'-(hexadecane-1,16-diylbis(azanediyl))bis(1-oxopropane-2,1-diyl)diisonicotinamide; N,N'-(2S,2'S)-1,1'-(octadecane-1,18-diylbis(azanediyl))bis(1-oxopropane-2,1-diyl)diisonicotinamide; N,N'-(2S,2'S)-1,1'-(ethane-1,2-diylbis(azanediyl))bis(1-oxo-3-phenylpropane-2,1-diyl)diisonicotinamide; N,N'-(2S,2'S)-1,1'-(propane-1,3-diylbis(azanediyl))bis(1-oxo-3-phenylpropane-2,1-diyl)diisonicotinamide; N,N'-(2S,2'S)-1,1'-(butane-1,4-diylbis(azanediyl))bis(1-oxo-3-phenylpropane-2,1-diyl)diisonicotinamide; N,N'-(2S,2'S)-1,1'-(pentane-1,5-diylbis(azanediyl))bis(1-oxo-3-phenylpropane-2,1-diyl)diisonicotinamide; N,N'-(2S,2'S)-1,1'-(hexane-1,6-diylbis(azanediyl))bis(1-oxo-3-phenylpropane-2,1-diyl)diisonicotinamide N,N'-(2S,2'S)-1,1'-(heptane-1,7-diylbis(azanediyl))bis(1-oxo-3-phenylpropane-2,1-diyl) diisonicotinamide; N,N'-(2S,2'S)-1,1'-(octane-1,8-diylbis(azanediyl))bis(1-oxo-3-phenylpropane-2,1-diyl) diisonicotinamide; N,N'-(2S,2'S)-1,1'-(nonane-1,9-diylbis(azanediyl))bis(1-oxo-3-phenylpropane-2,1-diyl) diisonicotinamide; N,N'-(2S,2' S)-1,1'-(decane-1,10-diylbis(azanediyl))bis(1-oxo-3-phenylpropane-2,1-diyl) diisonicotinamide; N,N'-(2S,2'S)-1,1'-(undecane-1,1'-diylbis(azanediyl))bis(1-oxo-3-phenylpropane-2,1-diyl) diisonicotinamide; N,N'-(2S,2'S)-1,1'-(dodecane-1,12-diylbis(azanediyl))bis(1-oxo-3-phenylpropane-2,1-diyl) diisonicotinamide; N,N'-(2S,2'S)-1,1'-(tridecane-1,13-diylbis(azanediyl))bis(1-oxo-3-phenylpropane-2,1-diyl) diisonicotinamide; N,N'-(2S,2'S)-1,1'-(tetradecane-1,14-diylbis(azanediyl))bis(1-oxo-3-phenylpropane-2,1-diyl) diisonicotinamide; N,N'-(2S,2'S)-1,1'-(hexadecane-1,16-diylbis(azanediyl))bis(1-oxo-3-phenylpropane-2,1-diyl) diisonicotinamide; N,N'-(2S,2'S)-1,1'-(octadecane-1,18-diylbis(azanediyl))bis(1-oxo-3-phenylpropane-2,1-diyl) diisonicotinamide; [1-12-[2-Benzyloxycarbonylamino-3-(1H-indol-3-yl)-propionylamino]-ethylcarbamoyl}-2-(1H-indol-3-yl)-ethyl]-carbamic acid benzyl ester; [1-{8-[2-Benzyloxycarbonylamino-3-(1H-indol-3-yl)-propionylamino]-octylcarbamoyl}-2-(1H-indol-3-yl)-ethyl]-carbamic acid benzyl ester; [1-13-[2-Benzyloxycarbonylamino-3-(1H-indol-3-yl)-propionylamino]-propylcarbamoyl}-2-(1H-indol-3-yl)-ethyl]-carbamic acid benzyl ester; [1-{9-[2-Benzyloxycarbonylamino-3-(1H-indol-3-yl)-propionylamino]-nonylcarbamoyl}-2-(1H-indol-3-yl)-ethyl]-carbamic acid benzyl ester; [1-{4-[2-Benzyloxycarbonylamino-3-(1H-indol-3-yl)-propionylamino]-butylcarbamoyl}-2-(1H-indol-3-yl)-ethyl]-carbamic acid benzyl ester; [1-[10-[2-Benzyloxycarbonylamino-3-(1H-indol-3-yl)-propionylamino]-decylcarbamoyl}-2-(1H-indol-3-yl)-ethyl]-carbamic acid benzyl ester; [1-15-[2-Benzyloxycarbonylamino-3-(1H-indol-3-yl)-propionylamino]-pentylcarbamoyl}-2-(1H-indol-3-yl)-ethyl]-carbamic acid benzyl ester; [1-{11-[2-Benzyloxycarbonylamino-3-(1H-indol-3-yl)-propionylamino]-undecylcarbamoyl}-2-(1H-indol-3-yl)-ethyl]-carbamic acid benzyl ester; [1-16-[2-Benzyloxycarbonylamino-3-(1H-indol-3-yl)-propionylamino]-hexylcarbamoyl}-2-(1H-indol-3-yl)-ethyl]-carbamic acid benzyl ester; [1-{12-[2-Benzyloxycarbonylamino-3-(1H-indol-3-yl)-propionylamino]-dodecylylcarbamoyl}-2-(1H-indol-3-yl)-ethyl]-carbamic acid benzyl ester; [1-{7-[2-Benzyloxycarbonylamino-3-(1H-indol-3-yl)-propionylamino]-heptylcarbamoyl}-2-(1H-indol-3-yl)-ethyl]-carbamic acid benzyl ester; N-[(1S)-2-methyl-1-[2-[[(2S)-3-methyl-2-(pyridine-4-carbonylamino)pentanoyl]amino]ethylcarbamoyl]butyl]pyridine-4-carboxamide; N-[(1S)-2-methyl-1-[8-[[(2S)-3-methyl-2-(pyridine-4-carbonylamino)pentanoyl]amino]octylcarbamoyl]butyl]pyridine-4-carboxamide; N-[(1S)-2-methyl-1-[3-[[(2S)-3-methyl-2-(pyridine-4-carbonylamino)pentanoyl]amino]propylcarbamoyl]butyl]pyridine-4-carboxamide; N-[(1S)-2-methyl-1-[9-[[(2S)-3-methyl-2-(pyridine-4-carbonylamino)pentanoyl]amino]nonylcarbamoyl]butyl]pyridine-4-carboxamide; N-[(1S)-2-methyl-1-[4-[[(2S)-3-methyl-2-(pyridine-4-carbonylamino)pentanoyl]amino]butylcarbamoyl]butyl]pyridine-4-carboxamide; N-[(1S)-2-methyl-1-[10-[[(2S)-3-methyl-2-(pyridine-4-carbonylamino)pentanoyl]amino]decylcarbamoyl]butyl]pyridine-4-carboxamide; N-[(1S)-2-methyl-1-[5-[[(2S)-3-methyl-2-(pyridine-4-carbonylamino)pentanoyl]amino]

pentylcarbamoyl]butyl]pyridine-4-carboxamide; N-[(1S)-2-methyl-1-[11-[[(2S)-3-methyl-2-(pyridine-4-carbonylamino)pentanoyl]amino]undecylcarbamoyl]butyl]pyridine-4-carboxamide; N-[(1S)-2-methyl-1-[6-[[(2S)-3-methyl-2-(pyridine-4-carbonylamino)pentanoyl]amino]hexylcarbamoyl]butyl]pyridine-4-carboxamide; N-[(1S)-2-methyl-1-[12-[[(2S)-3-methyl-2-(pyridine-4-carbonylamino)pentanoyl]amino]dodecylcarbamoyl]butyl]pyridine-4-carboxamide; N-[(1S)-2-methyl-1-[7-[[(2S)-3-methyl-2-(pyridine-4-carbonylamino)pentanoyl]amino]heptylcarbamoyl]butyl]pyridine-4-carboxamide; 4-(1H-imidazol-5-yl)-N-[(1S)-1-[2-[[(2S)-2-[[4-(1H-imidazol-5-yl)benzoyl]amino]-3-methyl-pentanoyl]amino]ethylcarbamoyl]-2-methyl-butyl]benzamide; 4-(1H-imidazol-5-yl)-N-[(1S)-1-[8-[[(2S)-2-[[4-(1H-imidazol-5-yl)benzoyl]amino]-3-methyl-pentanoyl]amino]octylcarbamoyl]-2-methyl-butyl]benzamide; 4-(1H-imidazol-5-yl)-N-[(1S)-1-[3-[[(2S)-2-[[4-(1H-imidazol-5-yl)benzoyl]amino]-3-methyl-pentanoyl]amino]propylcarbamoyl]-2-methyl-butyl]benzamide; 4-(1H-imidazol-5-yl)-N-[(1S)-1-[9-[[(2S)-2-[[4-(1H-imidazol-5-yl)benzoyl]amino]-3-methyl-pentanoyl]amino]nonylcarbamoyl]-2-methyl-butyl]benzamide; 4-(1H-imidazol-5-yl)-N-[(1S)-1-[4-[[(2S)-2-[[4-(1H-imidazol-5-yl)benzoyl]amino]-3-methyl-pentanoyl]amino]butylcarbamoyl]-2-methyl-butyl]benzamide; 4-(1H-imidazol-5-yl)-N-[(1S)-1-[10-[[(2S)-2-[[4-(1H-imidazol-5-yl)benzoyl]amino]-3-methyl-pentanoyl]amino]decylcarbamoyl]-2-methyl-butyl]benzamide; 4-(1H-imidazol-5-yl)-N-[(1S)-1-[5-[[(2S)-2-[[4-(1H-imidazol-5-yl)benzoyl]amino]-3-methyl-pentanoyl]amino]pentylcarbamoyl]-2-methyl-butyl]benzamide; 4-(1H-imidazol-5-yl)-N-[(1S)-1-[11-[[(2S)-2-[[4-(1H-imidazol-5-yl)benzoyl]amino]-3-methyl-pentanoyl]amino]undecylcarbamoyl]-2-methyl-butyl]benzamide; 4-(1H-imidazol-5-yl)-N-[(1S)-1-[6-[[(2S)-2-[[4-(1H-imidazol-5-yl)benzoyl]amino]-3-methyl-pentanoyl]amino]hexylcarbamoyl]-2-methyl-butyl]benzamide; 4-(1H-imidazol-5-yl)-N-[(1S)-1-[12-[[(2S)-2-[[4-(1H-imidazol-5-yl)benzoyl]amino]-3-methyl-pentanoyl]amino]dodecylcarbamoyl]-2-methyl-butyl]benzamide; 4-(1H-imidazol-5-yl)-N-[(1S)-1-[7-[[(2S)-2-[[4-(1H-imidazol-5-yl)benzoyl]amino]-3-methyl-pentanoyl]amino]heptylcarbamoyl]-2-methyl-butyl]benzamide; N-[(1S)-2-[[(1S)-1-[[(2R)-2-[[(2R)-2-benzamido-3-(1H-imidazol-5-yl)propanoyl]amino]-3-methyl-pentanoyl]amino]methylcarbamoyl]-2-methyl-butyl]amino]-1-(1H-imidazol-5-ylmethyl)-2-oxo-ethyl]benzamide; N-[(1R)-2-[[(1R)-1-[8-[[(2S)-2-[[(2S)-2-benzamido-3-(1H-imidazol-5-yl)propanoyl]amino]-3-methyl-pentanoyl]amino]octylcarbamoyl]-2-methyl-butyl]amino]-1-(1H-imidazol-5-ylmethyl)-2-oxo-ethyl]benzamide; N-[(1R)-2-[[(1R)-1-[3-[[(2S)-2-[[(2S)-2-benzamido-3-(1H-imidazol-5-yl)propanoyl]amino]-3-methyl-pentanoyl]amino]propylcarbamoyl]-2-methyl-butyl]amino]-1-(1H-imidazol-5-ylmethyl)-2-oxo-ethyl]benzamide; N-[(1R)-2-[[(1R)-1-[9-[[(2S)-2-[[(2S)-2-benzamido-3-(1H-imidazol-5-yl)propanoyl]amino]-3-methyl-pentanoyl]amino]nonylcarbamoyl]-2-methyl-butyl]amino]-1-(1H-imidazol-5-ylmethyl)-2-oxo-ethyl]benzamide; N-[(1R)-2-[[(1R)-1-[4-[[(2S)-2-[[(2S)-2-benzamido-3-(1H-imidazol-5-yl)propanoyl]amino]-3-methyl-pentanoyl]amino]butylcarbamoyl]-2-methyl-butyl]amino]-1-(1H-imidazol-5-ylmethyl)-2-oxo-ethyl]benzamide; N-[(1R)-2-[[(1R)-1-[10-[[(2S)-2-[[(2S)-2-benzamido-3-(1H-imidazol-5-yl)propanoyl]amino]-3-methyl-pentanoyl]amino]decylcarbamoyl]-2-methyl-butyl]amino]-1-(1H-imidazol-5-ylmethyl)-2-oxo-ethyl]benzamide; N-[(1R)-2-[[(1R)-1-[5-[[(2S)-2-[[(2S)-2-benzamido-3-(1H-imidazol-5-yl)propanoyl]amino]-3-methyl-pentanoyl]amino]pentylcarbamoyl]-2-methyl-butyl]amino]-1-(1H-imidazol-5-ylmethyl)-2-oxo-ethyl]benzamide; N-[(1R)-2-[[(1R)-1-[11-[[(2S)-2-[[(2S)-2-benzamido-3-(1H-imidazol-5-yl)propanoyl]amino]-3-methyl-pentanoyl]amino]undecylcarbamoyl]-2-methyl-butyl]amino]-1-(1H-imidazol-5-ylmethyl)-2-oxo-ethyl]benzamide; N-[(1R)-2-[[(1R)-1-[6-[[(2S)-2-[[(2S)-2-benzamido-3-(1H-imidazol-5-yl)propanoyl]amino]-3-methyl-pentanoyl]amino]hexylcarbamoyl]-2-methyl-butyl]amino]-1-(1H-imidazol-5-ylmethyl)-2-oxo-ethyl]benzamide; N-[(1R)-2-[[(1R)-1-[12-[[(2S)-2-[[(2S)-2-benzamido-3-(1H-imidazol-5-yl)propanoyl]amino]-3-methyl-pentanoyl]amino]dodecylcarbamoyl]-2-methyl-butyl]amino]-1-(1H-imidazol-5-ylmethyl)-2-oxo-ethyl]benzamide; N-[(1R)-2-[[(1R)-147-[[(2S)-2-[[(2S)-2-benzamido-3-(1H-imidazol-5-yl)propanoyl]amino]-3-methyl-pentanoyl]amino]heptylcarbamoyl]-2-methyl-butyl]amino]-1-(1H-imidazol-5-ylmethyl)-2-oxo-ethyl]benzamide; and mixtures thereof.

6. A method of structuring a consumer product composition comprising adding the pH tunable amido-gellant of claim 1 to the consumer product composition.

\* \* \* \* \*